(12) United States Patent
Taicher

(10) Patent No.: US 9,964,501 B2
(45) Date of Patent: May 8, 2018

(54) NUCLEAR MAGNETIC RESONANCE APPARATUS AND METHODS

(71) Applicant: Gersh Z. Taicher, Singapore (SG)

(72) Inventor: Gersh Z. Taicher, Singapore (SG)

( * ) Notice: Subject to any disclaimer, the term of this patent is extended or adjusted under 35 U.S.C. 154(b) by 641 days.

(21) Appl. No.: 14/533,121

(22) Filed: Nov. 5, 2014

(65) Prior Publication Data

US 2016/0124062 A1 May 5, 2016

(51) Int. Cl.

| | |
|---|---|
| *G01V 3/00* | (2006.01) |
| *G01N 24/08* | (2006.01) |
| *G01R 33/30* | (2006.01) |
| *G01R 33/38* | (2006.01) |
| *G01R 33/383* | (2006.01) |
| *G01R 33/341* | (2006.01) |

(52) U.S. Cl.
CPC ........... *G01N 24/08* (2013.01); *G01R 33/302* (2013.01); *G01R 33/383* (2013.01); *G01R 33/3808* (2013.01); *G01R 33/341* (2013.01)

(58) Field of Classification Search
USPC ......................................................... 324/309
See application file for complete search history.

(56) References Cited

U.S. PATENT DOCUMENTS

| | | |
|---|---|---|
| 4,710,713 A | 12/1987 | Taicher et al. |
| 4,717,877 A | 1/1988 | Taicher et al. |
| 4,717,878 A | 1/1988 | Taicher et al. |
| 4,933,638 A | 6/1990 | Kleingerg et al. |
| 5,055,787 A | 10/1991 | Kleinberg et al. |
| 5,698,979 A | 12/1997 | Taicher et al. |
| 6,091,241 A * | 7/2000 | Querleux ........... G01R 33/3808 324/300 |
| 6,208,142 B1 * | 3/2001 | Wagshul ........... G01R 33/3808 324/309 |
| 6,346,813 B1 | 2/2002 | Kleinberg |

(Continued)

FOREIGN PATENT DOCUMENTS

WO 2012118442 A1 9/2012

OTHER PUBLICATIONS

P.J. McDonald et al., "A unilateral NMR magnet for sub-structure analysis in the built environment: The Surface GAR Field", J. Mag. Res., 185 (2007) 1-11, Elsevier, Nov. 22, 2006.

(Continued)

*Primary Examiner* — Rodney Fuller
(74) *Attorney, Agent, or Firm* — Richard A. Fagin

(57) ABSTRACT

A nuclear magnetic resonance (NMR) apparatus includes at least one magnet configured to induce a static magnetic field in a sample of material to be analyzed, wherein the sample is disposed on one side of the at least one magnet. The at least one magnet is configured such that the static magnetic field induced in the sample of material to be analyzed is substantially planar along lines of equal static magnetic field amplitude. A method includes inducing a static magnetic field in a sample of material to be analyzed. The static magnetic field is substantially planar along surfaces of equal amplitude of the static magnetic field. The inducing originates on one side of the sample. A radio frequency magnetic field is induced in the sample substantially orthogonally to the static magnetic field. NMR phenomena excited in the sample are detected.

39 Claims, 26 Drawing Sheets

(56) References Cited

U.S. PATENT DOCUMENTS

| | | | |
|---|---|---|---|
| 6,489,872 B1* | 12/2002 | Fukushima | G01R 33/383 |
| | | | 335/216 |
| 6,977,503 B2 | 12/2005 | Prado | |
| 7,355,402 B1 | 4/2008 | Taicher et al. | |
| 7,358,734 B2 | 4/2008 | Blumich et al. | |
| 7,366,559 B2 | 4/2008 | Taicher et al. | |
| 7,366,560 B2 | 4/2008 | Taicher et al. | |
| 8,334,693 B2 | 12/2012 | Lee | |
| 8,519,708 B2 | 8/2013 | Prado et al. | |
| 8,704,517 B2 | 4/2014 | Lee | |
| 2003/0141871 A1* | 7/2003 | Marek | G01R 33/34061 |
| | | | 324/320 |
| 2004/0066194 A1* | 4/2004 | Slade | G01R 33/3808 |
| | | | 324/318 |
| 2010/0102811 A1* | 4/2010 | Demas | G01R 33/3808 |
| | | | 324/309 |
| 2012/0010497 A1* | 1/2012 | Ehman | G01R 33/3806 |
| | | | 600/410 |
| 2014/0152302 A1* | 6/2014 | Rapoport | G01R 33/3802 |
| | | | 324/307 |
| 2014/0225611 A1* | 8/2014 | Rapoport | G01R 33/3802 |
| | | | 324/309 |
| 2015/0212225 A1* | 7/2015 | Reiderman | G01N 24/081 |
| | | | 324/303 |
| 2015/0369886 A1* | 12/2015 | Menon | G01R 33/365 |
| | | | 324/322 |
| 2017/0176550 A1* | 6/2017 | Song | G01R 33/341 |

OTHER PUBLICATIONS

Marble, Andrew E. et al., "An analytical methodology for magnetic field control in unilateral NMR", J. Mag. Res. 174 (2005) 78-87.

G. Eidmann, et. al., "The NMR MOUSE, a Mobile Universal Surface Explorer", J. Mag. Res., Series A 122, 104-109 (1996) Article No. 0185.

* cited by examiner

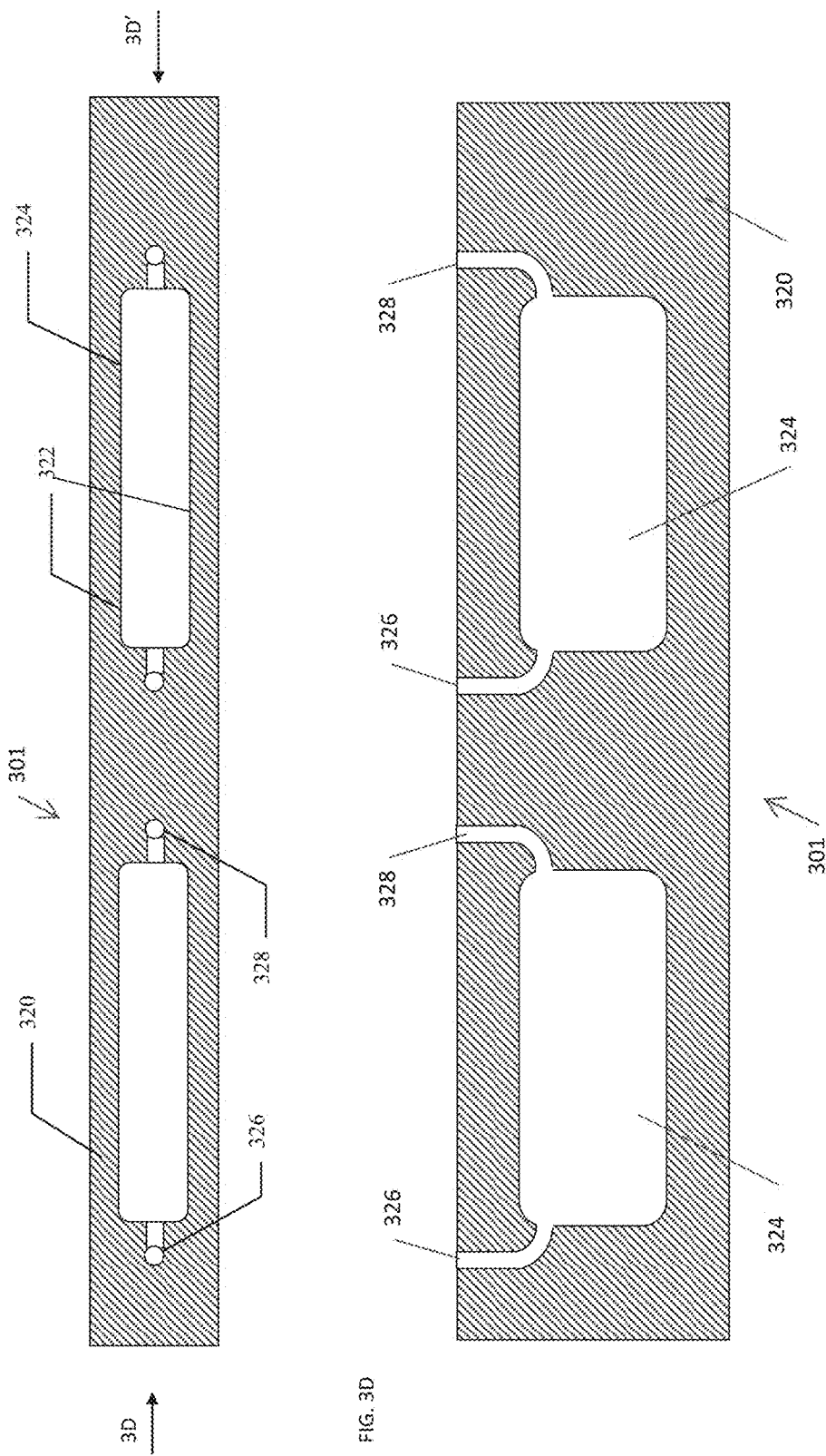

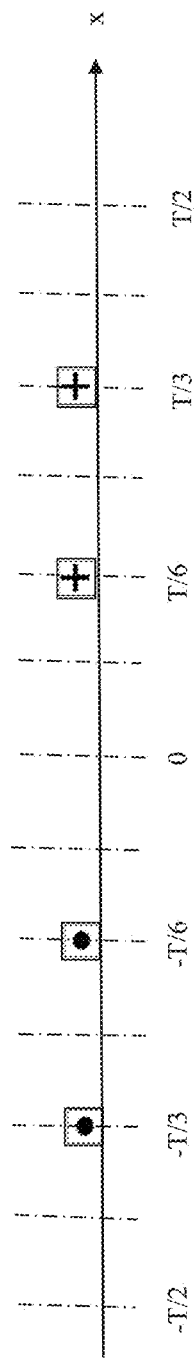

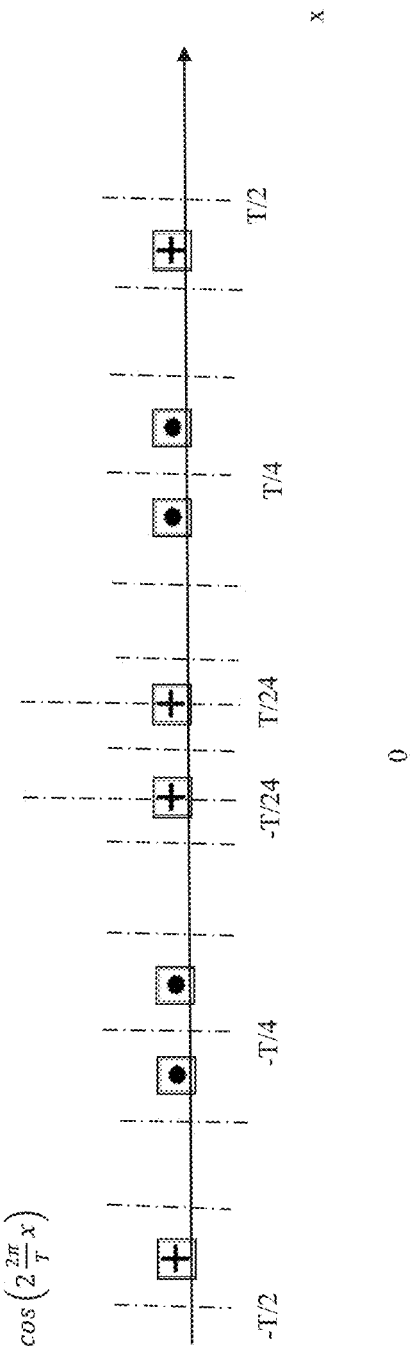

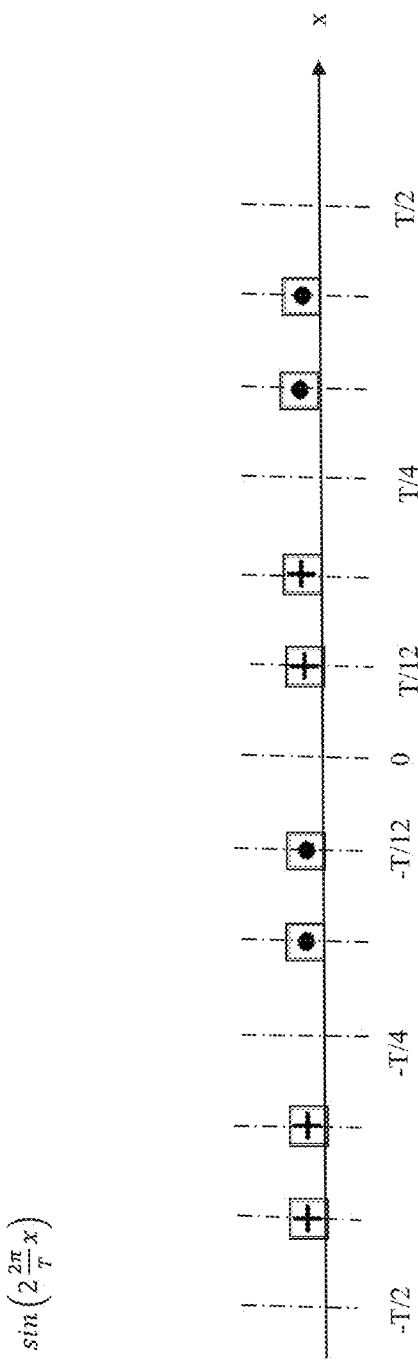

NUCLEAR MAGNETIC RESONANCE APPARATUS AND METHODS

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND

This disclosure is related to the field of nuclear magnetic resonance (NMR) apparatus and methods. More specifically, the disclosure is related to NMR apparatus configured for measurement of surface and bulk NMR properties of very small liquid samples, for example, to detect the presence of certain substances in the very small liquid sample.

More particularly, the disclosure relates to methods and apparatus for using NMR for differentiation of fluid properties in the bulk of a fluid sample and in a layer of the fluid that interacts with a surface. In one aspect, methods and apparatus according to the disclosure relate to using NMR for rapid quantitative determination of cell conjugation. In another example aspect, methods and apparatus according to the disclosure relate to using NMR in toxicology as a rapid presumptive screen for certain classes of drugs. In yet another aspect, methods and apparatus according to the disclosure relate to using NMR in disease diagnosis to evaluate either the presence of an antigen or the presence of an antibody in a serum or other fluid sample.

The description herein and its background will be approached in the context of detecting the presence of an antigen in a sample. There is no intention to limit the generality of the present disclosure to the field of detecting the presence of an antigen in a sample.

Enzyme-linked immunosorbent assay (ELISA) is a test that uses antibodies and color change to identify a substance. In direct-ELISA a labeled primary antibody reacts directly with an antigen. Indirect-ELISA uses an unlabeled primary antibody in conjunction with a labeled secondary antibody. Since the labeled secondary antibody is directed against all antibodies of a given species, Indirect ELISA can be used with a wide variety of primary antibodies.

Antibody-sandwich ELISAs is a very useful type of immunosorbent assay for detecting antigens because they are frequently between 2 and 5 times more sensitive than those in which the antigen is directly bound to a solid phase. To detect the antigen, wells of microtiter-sample size plates (typically having volume of about ⅓ cubic centimeter and coated surface of about 1 square centimeter) are coated with a specific (capture) antibody followed by incubation with test solutions containing an antigen. Unbound antigen is washed out and an antigen-specific antibody is conjugated to an enzyme (i.e., a developing reagent) is added, followed by another incubation. Enzyme labeled antibody can be produced in a laboratory animal that produces passively adsorbed antibody, or from a different species immunized with the same antigen that is captured. Unbound conjugate is washed out and a substrate is added. After another incubation, the degree of substrate hydrolysis is measured. The amount of substrate hydrolyzed is proportional to the amount of antigen in the test solution.

NMR signals as used in methods according to the present disclosure arise from the nuclei of hydrogen atoms in water molecules. Once generated, the magnitude of the NMR signal decays according to transverse (T2) and longitudinal (T1) relaxation properties of the water-containing material being analyzed. Spin-spin (T2) relaxation occurs when a given ensemble of oscillating hydrogen nuclear axis spins lose coherence. Loss of spin coherence is caused by macroscopic and microscopic fluctuations in the static magnetic field experienced by a freely diffusing nuclear axis spin. The former is commonly referred to as T2* relaxation and the latter as T2 relaxation. T2 relaxation contains information about the microscopic environment experienced by the hydrogen nuclei in the water-containing material. T2 relaxation can be measured independently from T2* by means of a specialized series of RF pulses and delays, called a CPMG (Can Purcell Meiboom Gill) pulse sequence. A CPMG pulse sequence removes the effects of static magnetic field macroscopic inhomogeneities to specifically measure the contribution from the microscopic environment, by creating a series of spin echoes. The relaxation time is significantly shorter for a molecule proximate a sample chamber surface or wall area, as compared to a molecule in the bulk volume. This is typically an effect of paramagnetic centers at a wall surface that causes the relaxation time to be shorter.

T2 measurements can be carried out in real time during an analyte-induced response. T2 changes as a function of measurement time and the rate of T2 change can be correlated to a quantitative amount of analyte. The measured T2 values can be influenced by several assay, instrument, measurement, and processing parameters. For example, the measured T2 values may depend on the static magnetic field strength and homogeneity and the total spin echo measurement time. Additional parameters and variables may include valency and size of the analyte, and sample temperature. As a result, T2 values may increase or decrease with time.

Sample mixing and loading, as well as T2 measurements, can be completed in tens of seconds, making sample incubation the rate-limiting step for magnetic resonance switching (MRSw) measurements. Incubation times may be as long as several hundreds of minutes. NMR measurement of spin-lattice (T1) relaxation and diffusion can be completed in few minutes that is longer than T2 measurement, but can provide valuable information related to fluid-surface interaction.

BRIEF DESCRIPTION OF THE DRAWINGS

FIGS. 3D and 3E show side and top views, respectively, of the multiple sample holder of FIG. 3C.

FIGS. 13A, 13B, 13C and 13D provide details for examples of orthogonal shimming.

DETAILED DESCRIPTION

Figure 1:
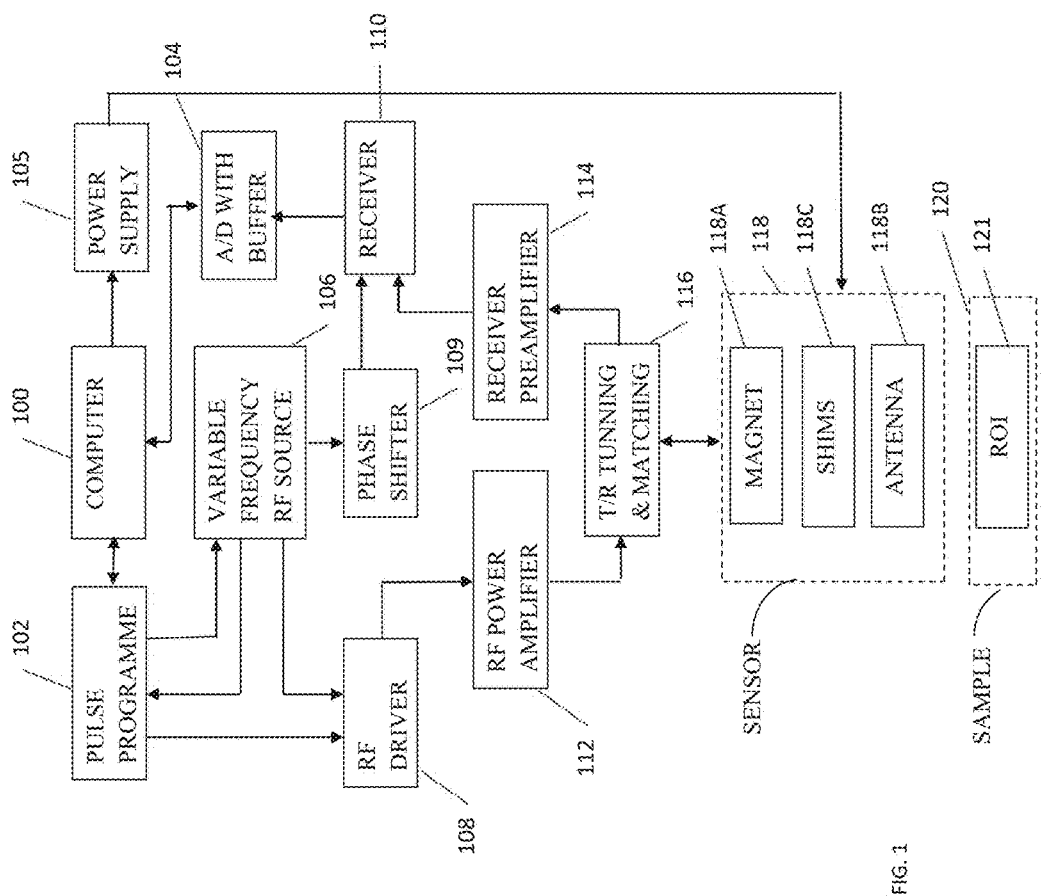
FIG. 1 is a functional block diagram of an example nuclear magnetic resonance (NMR) sensing apparatus.

FIG. 1 shows a functional block diagram of a nuclear magnetic resonance (NMR) apparatus that may be used in some embodiments. A transmitter/receiver (T/R) tuning and matching circuit 116 may be directly connected, or electromagnetically coupled to a sensor 118. The T/R tuning and matching circuit 116 typically includes a series of resonance capacitors (not shown separately), a transmitter/receiver switch (not shown separately) and both "to-transmitter" and "to-receiver" matching circuitry. The T/R tuning and matching circuit 116 may be coupled both to a radio frequency (RF) power amplifier 112 and to a receiver preamplifier 114. The locations of the T/R tuning and matching circuit 116, the RF power amplifier 112 and the receiver preamplifier 114 relative to the sensor 118 are not to be construed as a limitation on the scope of the present disclosure.

Part of the control circuitry for the NMR instrument may include a processor or computer 100, which among other functions may provide control signals to a pulse programmer 102. The processor or computer 100 may be implemented in any known manner, including, without limitation as a field programmable gate array, electrically erasable read only memory, microprocessor, application specific integrated circuit, digital signal processor or the like. The pulse programmer 102 controls the timing and operation of a variable frequency RF signal source 106. An RF driver 108 receives an input from the pulse programmer 102 and from the variable frequency RF source 106 and provides an output to the RF power amplifier 112. The pulse programmer 102 is synchronized with the variable frequency RF source 106. The RF power amplifier 112 provides a high power signal to drive a transceiver antenna 118B for generating an RF magnetic field in a sensitive volume to be further described in detail below. The RF power amplifier 112 may be directly connected (typically by a switch in the T/R tuning and matching circuit 116) to the transceiver antenna 118B during transmission of RF power pulses, or may be electromagnetically coupled.

During detection of induced NMR signals, the transceiver antenna 118B can be electrically connected to the receiver preamplifier 114 by means of the switch in the T/R tuning and matching circuit 116. The output of the RF receiver preamplifier 114 may be provided to an RF receiver 110. The RF receiver 110 also receives a phase reference input from a phase shifter 109. The phase shifter 109 receives a primary phase reference input from the variable frequency RF source 106. The RF receiver 110 may include quadrature detection. The RF receiver 110 provides an output to an A/D converter and buffer 104 that is synchronized with the processor or computer 100. In some embodiments several sensors configured as explained above, each corresponding to a different NMR region of interest may be used sequentially, each being switched on and off by the T/R tuning and matching circuit 116. One example may use a 96 well microtiter plate, a standard tool in analytical research and clinical diagnostic testing laboratories.

Various embodiments of the sensor 118, which will be set forth in more detail below, generally include at least one magnet 118A such as a permanent magnet or an electromagnet to induce a static magnetic field having well known amplitude and direction distribution. The antenna 118B may be one or more wire coils, as will be further explained below, to induce an RF magnetic field having a known amplitude and direction distribution and to detect NMR signals induced in a sample 120 being analyzed. The sample 120 is generally disposed within a NMR region of investigation (ROI) 121, in which the amplitude of the static magnetic field and the frequency of the RF magnetic field are selected to excite NMR phenomena within the sample 120.

In some embodiments, the magnet 118A may include shimming electromagnets 118C connected to a power supply 105 which receives an input from the processor or computer 100. The shimming electromagnets 118C may be used to adjust distribution of the static magnetic field induced by the magnet 118A. The magnet 118A and the shimming electromagnets 118C may be a part of the sensor 118 or may be disposed remotely but in close proximity to the antenna 118C.

In the description of various embodiments of an NMR apparatus according to the present disclosure, reference will be made to one or more magnets magnetized in a particular direction. Depending on the particular arrangement of the one or more magnets, the amplitude distribution and the direction distribution of the resulting static magnetic field may vary within any plane normal to what will be defined herein as a longitudinal axis of the apparatus. The length of the one or more magnets may be selected such that within a defined distance along the longitudinal axis, the amplitude distribution and the magnetization distribution are substantially constant within the defined distance. In a similar manner, one or more radio frequency antennas may be configured to have a magnetic dipole moment orthogonal to the static magnetic field direction, however the antenna sensitivity along the longitudinal axis may be substantially constant within a selected distance along the longitudinal axis. Finally, a sample chamber may be disposed within the static magnetic field and within the radio frequency magnetic field and/or the detection region defined by the one or more radio frequency antennas such that the length of the sample chamber along the longitudinal axis is disposed entirely within the selected distance defined by the one or more radio frequency antennas.

The system explained with reference to FIG. 1 may be used to excite NMR phenomena in a sample of material to be analyzed and may measure NMR induced signals emitted by the NMR phenomena excited in the sample. As explained in the Background section herein, NMR signals as used in methods according to the present disclosure arise from selected nuclei, for example, hydrogen atoms in water molecules. Once generated, the magnitude of the NMR signal decays according to transverse (T2) and longitudinal (T1) relaxation properties of the water-containing material being analyzed. Spin-spin (T2) relaxation occurs when a given ensemble of oscillating hydrogen nuclear axis spins lose coherence. Loss of spin coherence is caused by macroscopic and microscopic fluctuations in the static magnetic field experienced by a freely diffusing nuclear axis spin. The former is commonly referred to as T2* relaxation and the latter as T2 relaxation. T2 relaxation contains information about the microscopic environment experienced by the hydrogen nuclei in the water-containing material. T2 relaxation can be measured independently from T2* by means of a specialized series of RF pulses and delays, called a CPMG (Carr Purcell Meiboom Gill) pulse sequence. A CPMG pulse sequence removes the effects of static magnetic field inhomogeneities to specifically measure the contribution from the microscopic environment by creating a series of nuclear magnetic axial spin echoes. The relaxation time is significantly shorter for a molecule proximate a sample chamber surface or wall area, as compared to a molecule in the bulk volume. This is typically an effect of paramagnetic centers at a wall surface that causes the relaxation time to be shorter.

In embodiments to be described in more detail below, the static magnetic field and a gradient of the amplitude of the static magnetic field are substantially perpendicular to a longitudinal axis. In embodiments to be described in more detail below, an amplitude of the static magnetic field within the ROI within the sample of material to be analyzed is substantially homogeneous.

In some embodiments to be described in more detail below, the gradient of the amplitude of the static magnetic field within the ROI within the sample is homogeneous and uniform.

In some embodiments to be described in more detail below, the static magnetic field within the ROI within the sample is polarized in one of directions perpendicular and parallel to a plane along lines of equal static magnetic field amplitude.

Figure 2:
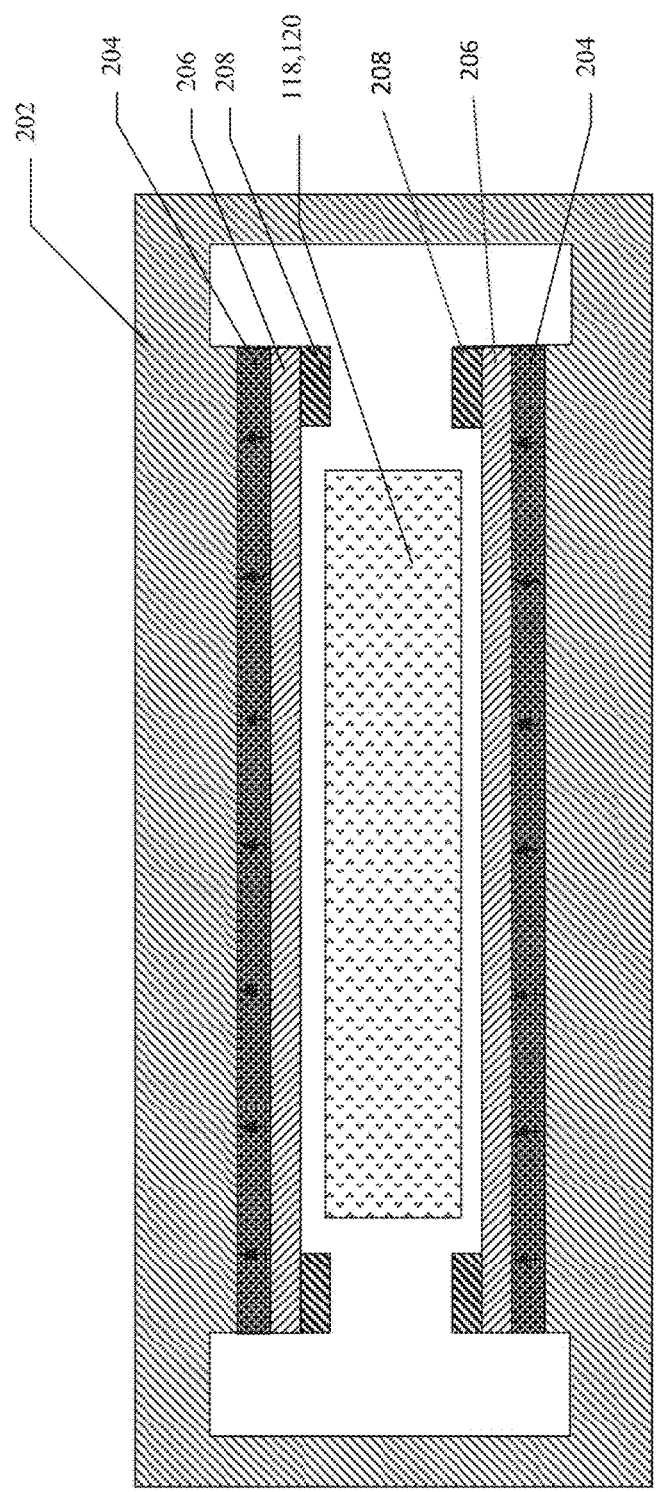
FIG. 2 shows an example embodiment of magnet, sensor and sample chamber.

FIG. 2 shows one example embodiment of magnets, a sensor and sample chamber. Permanent magnets 204 may be disposed on opposite sides of a sensor 118 and sample chamber 120. The permanent magnets 204 may be polarized along the direction shown by the arrows so that the space in between the permanent magnets 204 has a substantially homogeneous and uniform static magnetic field. A flux closure 202 may enclose the permanent magnets 204. Magnetic pole pieces 206 which may be made from magnetically permeable material, may be disposed on the inner surface of each magnet 204. Magnetically permeable material shims 208 may be disposed at the longitudinal ends of each pole piece 206 to further correct the shape of the static magnetic field between the permanent magnets 204 so that the static magnetic field is substantially uniform in direction and amplitude between the magnets where a sensor and sample 118, 120 are disposed.

Figure 3A:
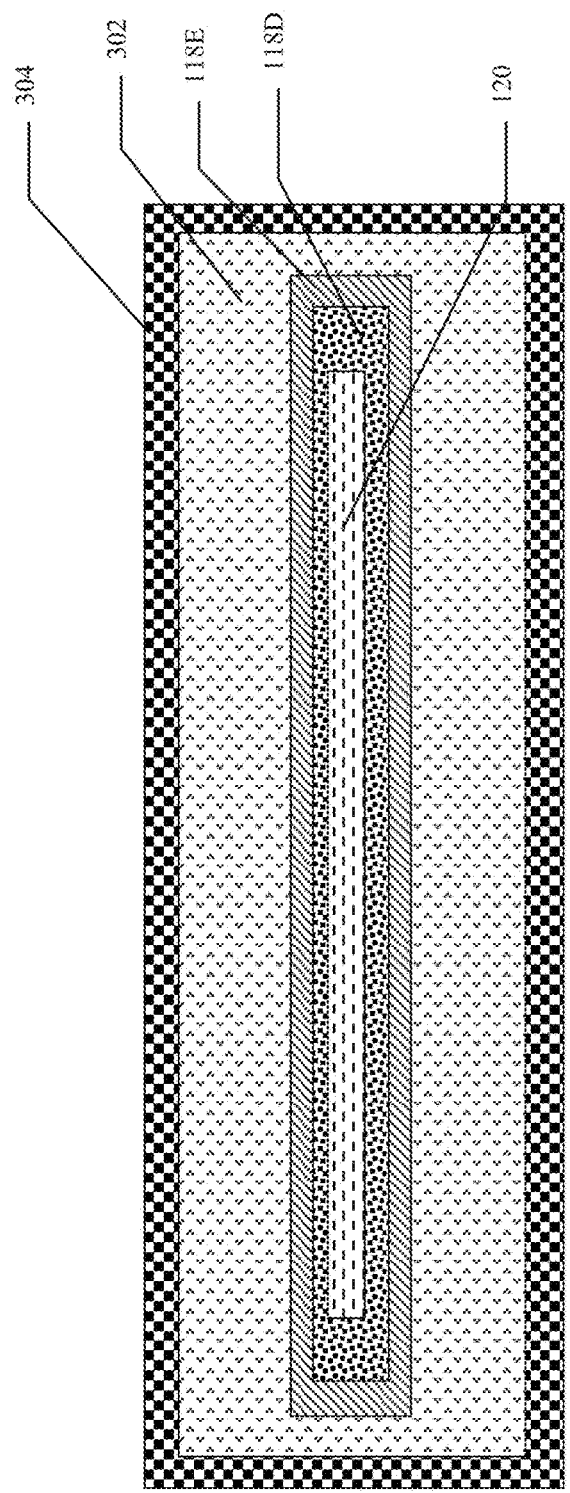
FIG. 3A shows an example sensor and sample chamber in more detail.
Figure 3B:
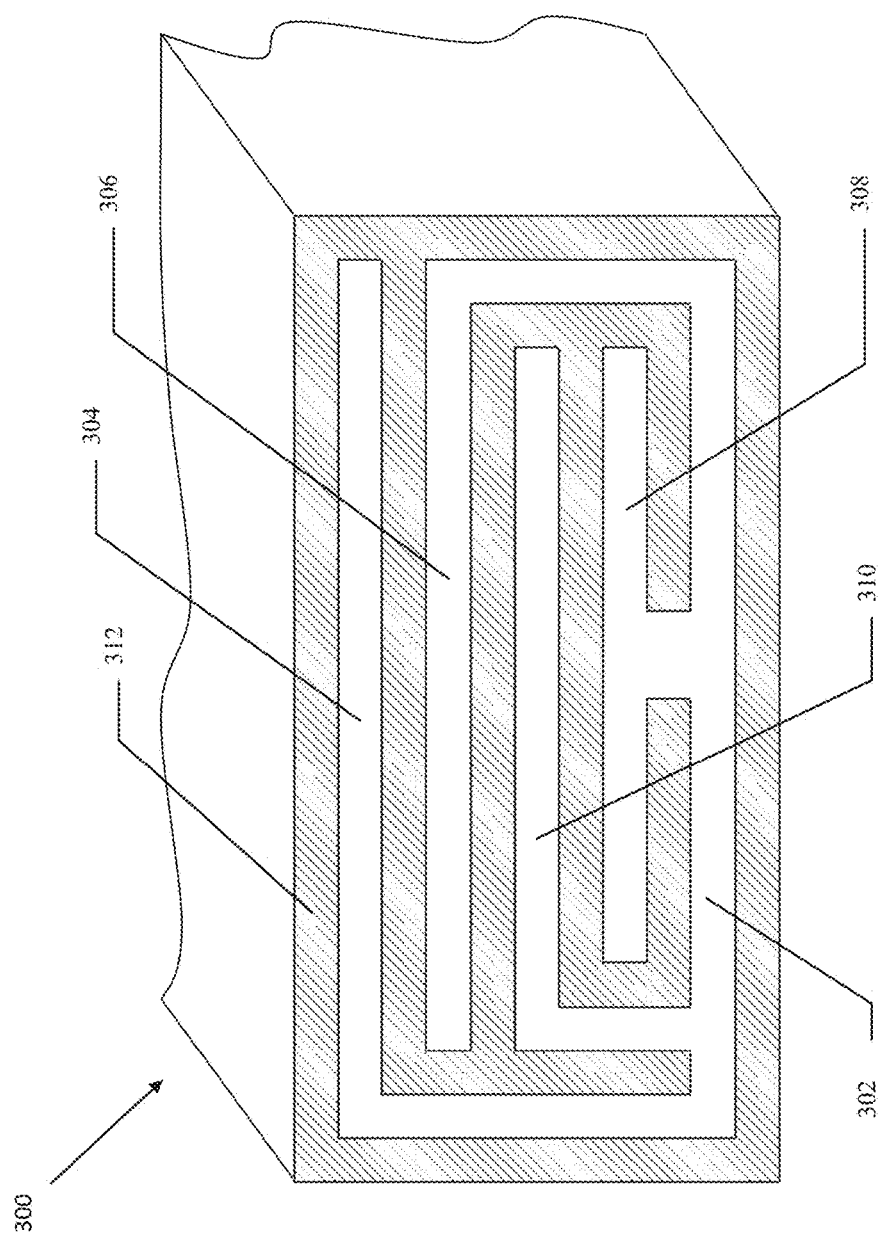
FIG. 3B shows an example of a 3-dimensional multilayer microfluidic device.

FIG. 3A shows the sensor and sample of FIG. 2 in more detail. A protective cover 118D, such as may be made from glass or plastic such as polystyrene may define an opening or chamber in which the sample 120 may be inserted. In some embodiments, the opening or chamber may be in one of ranges less than 10, 10 to 50, 50 to 100, 100 to 300, and 300 to 1000 microns in thickness so that NMR experiments performed on the sample 120 will be substantially entirely affected by surface contact effects between the sample 120 and the protective cover 118D. The choice is the range of the chamber thickness may depend on molecule or cell size being analyzed. In other embodiments the sample (i.e., the opening or chamber) thickness may be on the order, for example, of one to ten millimeters, but the fluid inside the sample holder may be evenly separated by very thin plates. This will result in high surface to volume ratio and a fluid layer being only a fraction of the opening or chamber thickness. An example embodiment of how to construct such a layered sample is described in, Andres W. Martinez, Scott T. Phillips, and George M. Whitesides, *Three-dimensional microfluidic devices fabricated in layered paper and tape*, Proceedings of the National Academy of Sciences of the United States of America, vol. 105, no. 50, pp. 19606-19611, (Dec. 16, 2008). FIG. 3B shows an example of one implementation of 3-dimensional multilayer sample.

The RF antenna 118E may be disposed around the exterior of the protective cover 118D. A glass or plastic cover 302 may be disposed around the exterior of the antenna 118E. A radio frequency (RF) magnetic shield 304 may be disposed externally to the cover 302. The RF shield 304 may be made from an electrically conductive, non-magnetic material such as copper, so that the RF magnetic field induced by the antenna 118E is substantially entirely contained within the RF shield 304.

Figure 4:
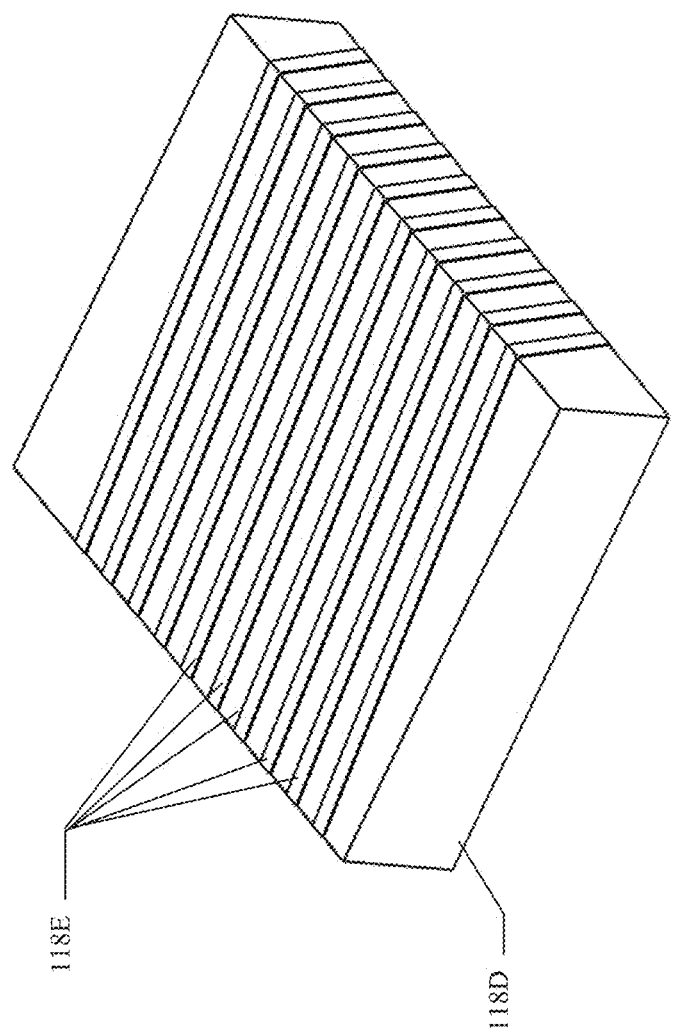
FIG. 4 shows an example antenna wound around the exterior of a sample cover of the example embodiment of FIG. 3.

FIG. 4 shows an oblique view of the protective cover 118D and the RF antenna 118E. The RF antenna 118E may be wound in the form of a flat solenoid on the exterior of the sample cover 118D so that RF magnetic fields induced in the sample (120 in FIG. 3A) are substantially transverse to the static magnetic field induced by the magnets (FIG. 2) and are substantially uniform in direction and amplitude.

The embodiments explained with reference to FIGS. 2, 3 and 4 are for analysis of samples entirely within a magnet and antenna structure for the purpose of obtaining NMR measurements in a substantially homogeneous static magnetic field. Measurements of surface related effects on the sample being analyzed may be obtained, in some embodiments, by limiting the thickness of the sample or selecting a sample volume to surface area ratio such that substantially all of the sample volume is in contact with a surface of the sample chamber.

Example embodiments of NMR apparatus for imaging within different regions of interest in a sample placed to one side of the apparatus will now be explained with reference to FIGS. 5 through 20. A common attribute of the example embodiments in FIGS. 5 through 20 is an arrangement of one or more magnets and/or pole pieces that induce a static magnetic field that is substantially flat along lines of equal static magnetic field amplitude, wherein the static magnetic field amplitude decreases with respect to linear distance from the surface of the magnet structure. Antenna structures may be disposed between the surface of the magnet structure and the edge of a sample (which for purposes of the present description may be thought of as an infinite half-space sample) which induce RF magnetic fields having a predetermine amplitude and direction distribution, but substantially an equal amplitude and a orthogonal direction at each point within a ROI to the orientation of the static magnetic field. In some embodiments, the frequency of the RF magnetic field may be selected to induce NMR phenomena in ROI at a selected distance from the edge of the sample. Correspondingly, a bandwidth of the RF magnetic field and the RF receiver may be selected so that the ROI is a selected thickness, depending on the static magnetic field gradient at the selected distance from the edge of the sample.

In the example embodiments to be explained with reference to FIGS. 5 through 20, a planar cross section is shown in a direction along the longitudinal axis as described above. Embodiments of an apparatus according to the present disclosure may extend in a direction transverse to the planar cross-section shown in the various figures to an extent such that a static magnetic field induced in the sample is substantially uniform in amplitude and polarization direction along the direction transverse to the illustrated cross-sections. Similarly, antenna structures shown in the figures may have an extent along the direction transverse to the plane of the cross sections such that an RF magnetic field induced in the sample by the antenna structures is also substantially uniform in amplitude and polarization direction within the sample.

Figure 5:
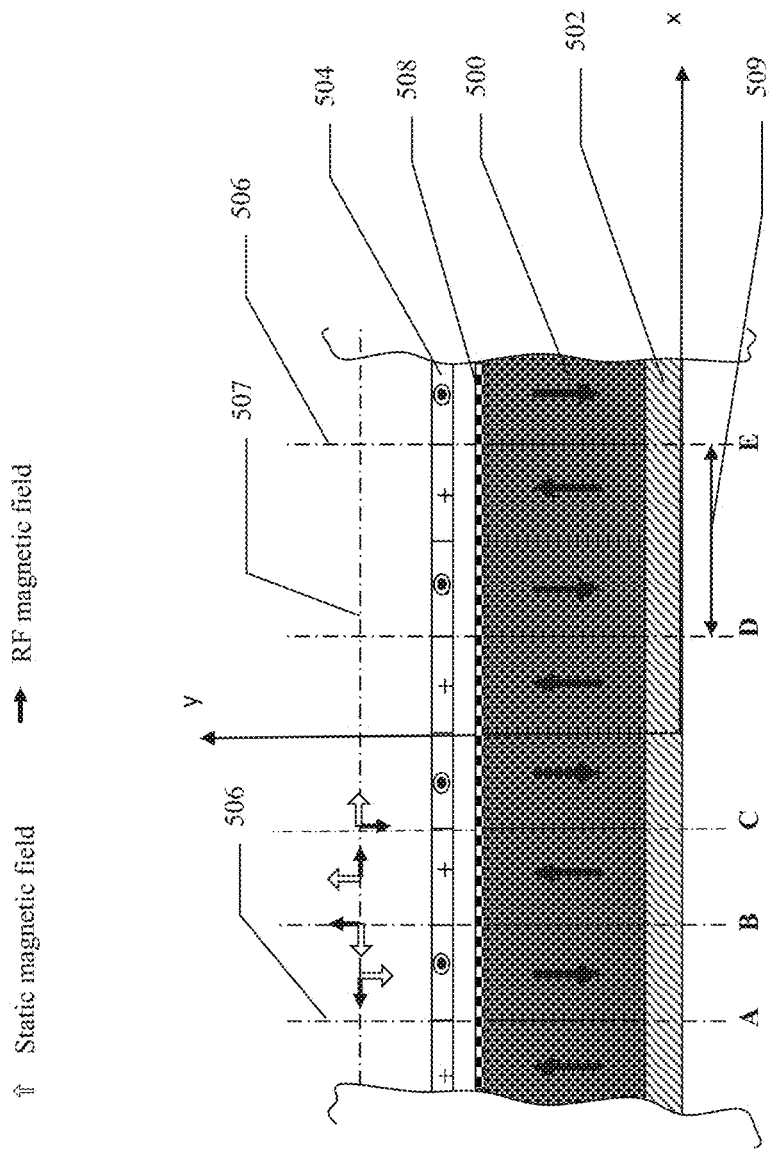
FIG. 5 shows an example embodiment of periodic magnets and antennas for disposing a sample to one side of the sensor.

FIG. 5 shows a conceptual example of an infinite (with respect to a third dimension) two-dimensional periodic permanent magnet and antenna structure. Permanent magnets 500 may be arranged adjacent to each other and in alternating polarity as indicated by the arrows thereon. One side of the magnets 500 may be in contact with a flux closure 502 such as may be made from low carbon steel or other highly magnetically permeable material. All of the magnets 500 in the present example have uniform magnetization in a direction perpendicular to the surface of the magnets 500. The static magnetic field will have substantially constant amplitude in planes parallel to a surface of the magnets but periodically varying in direction along a direction parallel to the surface of the magnets 500. The static magnetic field components in y direction which is perpendicular to the surface of the magnets 500 varying sinusoidally with position along x direction which is parallel to the surface of the magnets 500, and the static magnetic field components in x direction varying cosinusoidally with position along the x direction. Magnetization of the magnets 500 may be represented by the expression:

$$M_y = M_0 \sin\left(\frac{2\pi}{T}x\right); M_x = 0; \tag{1}$$

where $M_0$ represents the magnets' maximum magnetization, Mx and My represent the magnetization in the x and y directions (in the horizontal and vertical directions, respectively in the plane of FIG. 5, wherein the z direction is perpendicular to the plane of FIG. 5) and T is the period 509.

The foregoing arrangement of magnets 500 as stared above produces a sinusoidally varying y-component and a cosinusoidally varying x-component of the static magnetic field having substantially constant amplitude along lines parallel to the surface of the magnets 500 at any linear distance therefrom. The static magnetic field for all positive values of y may be expressed as:

$$B_y = B_0 \sin\left(\frac{2\pi}{T}x\right)e^{-\frac{2\pi}{T}y}; B_x = B_0 \cos\left(\frac{2\pi}{T}x\right)e^{-\frac{2\pi}{T}y}; \tag{2}$$

$$|B| = B_0 e^{-\frac{2\pi}{T}y}$$

where |B| is the static magnetic field amplitude.

The orientation of the static magnetic field along a line 507 parallel to the surface of the magnets 500 is shown by the open arrows. Current flow in an RF antenna 504 is indicated by polarity symbols (+) and (●). The current in the RF antenna 504 has a surface current density Jz sinusoidally varying along a x direction parallel to the surface of the magnets 500:

$$J_z = J_0 \sin\left(\frac{2\pi}{T}x\right) \tag{3}$$

The RF antenna 504 may be disposed between a surface of the magnets 500 and a sample to be analyzed (explained with reference to FIG. 9). Presence of electrically conductive permanent magnet material in the vicinity of the RF antenna 504 may distort the RF magnetic field, induce eddy current losses, and eventually cause extra noise during reception of NMR signals. A highly electrically conductive, non-magnetic shield 508, which may be made of thin sheet copper or similar material may be placed on the surface of the magnets 500 as shown in FIG. 5. The orientation of the RF magnetic field is indicated by the filled (black) arrows, and is at every point along the line 507 parallel to the surface of the magnets 500 and orthogonal to the static magnetic field induced by the magnets 500.

$$H_y = H_0 \cos\left(\frac{2\pi}{T}x\right)e^{-\frac{2\pi}{T}y}; H_x = H_0 \sin\left(\frac{2\pi}{T}x\right)e^{-\frac{2\pi}{T}y}; \tag{4}$$

$$|H| = H_0 e^{-\frac{2\pi}{T}y}$$

where |H| is the RF magnetic field amplitude.

Lines of zero static magnetic field potential 506 are shown at A, B, C, D and E. By placing steel or other highly magnetically permeable material along any pair of zero magnetic potential lines, the static magnetic field in the space between such lines will not be affected. For example, a half period permanent magnet structure will be further explained with reference to FIG. 11 and a one period permanent magnet structure will be further explained with reference to FIG. 12.

The lines 506 shown at A, B, C, D and E have a normal component of the RF magnetic field equal to zero and therefore by placing highly electrically conductive material such as copper along any pair of zero normal component lines of the RF magnetic field, an RF magnetic field in space between such lines will not be affected. For example, the half period permanent magnet structure will be further explained with reference to FIG. 11 and the one period permanent magnet structure will be further explained with reference to FIG. 12. Placing copper or similar non-magnetic, electrically conductive sheets along the lines 506 will slightly alter the period of the RF magnetic field as compared to the static magnetic field. However, the sheet thickness may be much less than 1 mm since the required thickness may be only several multiples of the Skin Depth. Thus, for example, at an RF frequency of 5 MHz the skin depth for copper is about. 0.029 mm.

In general, for any magnetization and current distribution at y<0, the resulting static magnetic field and RF magnetic field for y>0 in the Cartesian coordinate system is a sum of solutions of Laplace's equation for the $B_x$ and $B_y$ static magnetic field components. In terms of harmonic functions it takes the form:

$$B_x = \sum_{n=1}^{\infty}\left[A_n\cos\left(n\frac{2\pi}{T}x\right) + B_n\sin\left(n\frac{2\pi}{T}x\right)\right]e^{-n\frac{2\pi}{T}y} \quad (5)$$

$$B_y = \sum_{n=1}^{\infty}\left[C_n\cos\left(n\frac{2\pi}{T}x\right) + D_n\sin\left(n\frac{2\pi}{T}x\right)\right]e^{-n\frac{2\pi}{T}y} \quad (6)$$

where $A_n;B_n;C_n;D_n$ are constants, T is a period and n is an integer wavenumber.

In the conceptual example shown in FIG. 5, for n=1 $A=A_1=D_1\neq 0$; $B_1=0$; $C_1=0$; and for n>1 $A_n=0$; $B_n=0$; $C_n=0$; $D_n=0$; or for n=1 $A=B_1=C_1\neq 0$; $A_1=0$; $D_1=0$; and for n>1 $A_n=0$; $B_n=0$; $C_n=0$; $D_n=0$; the static magnetic field amplitude |B| takes the form:

$$|B| = Ae^{-\frac{2\pi}{T}y}; \quad (7)$$

In practice this is not practicable. It is important to note that for large values of n (the higher order magnetic field harmonics) the decay with the distance from the magnetic field source is much faster than for the first harmonic and lower order harmonics. Therefore, it is preferable that for small values of n (except 1), for example the values two and three, at least, C and D are theoretically zero and will as a practical matter be substantially zero, where the higher order harmonics, for example four and above, will be close to zero due to decay in the region of investigation—ROI (121 in FIG. 10).

For each specific geometrical configuration of magnets and RF antenna currents all geometrical parameters may be selected to nullify the required harmonics. This general orthogonal approach will be shown in detail and may be applied to specific designs of magnets, RF antennas, and DC current (electromagnet) shims, ferromagnetic shims, or permanent magnet shims.

Figures 6A, 6B:
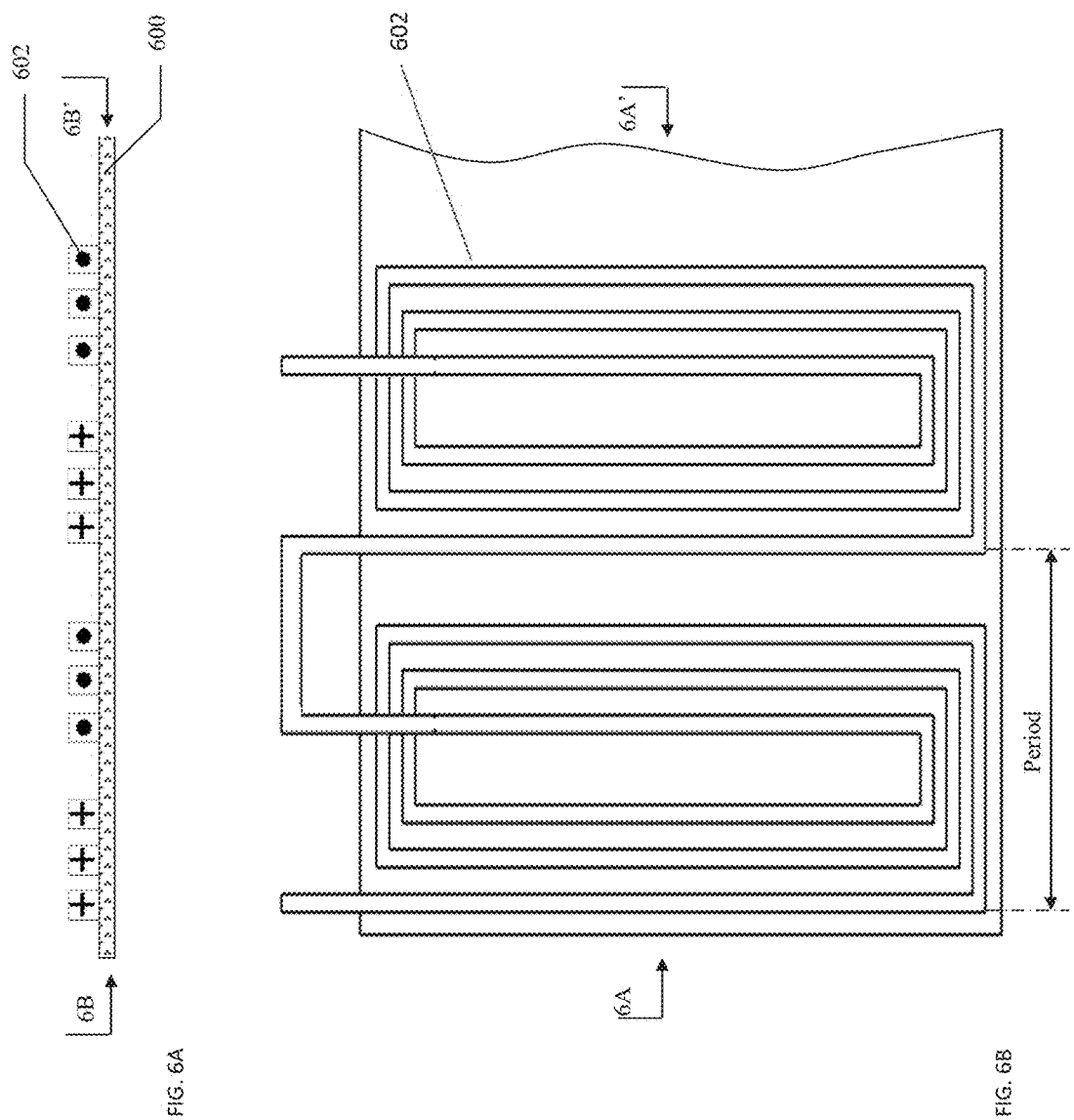
FIGS. 6A and 6B show side and plan views, respectively, of the example antenna of the embodiment of FIG. 5.

FIG. 6A shows a side view of an RF antenna arrangement that may be used in the embodiment of FIG. 5. Wires wound into loops (FIG. 6B) are shown at 602, wherein relative current flow polarity therein is indicated by symbols (+) and (●). The wire loops 602 may be disposed on an electrically non-conductive, non-magnetic material plate 600 such as may be made from plastic or glass.

FIG. 6B shows a plan view an example of how the antenna coils 602 may be wound. The antenna coils 602 may be wound to have one set of positive polarity lines and one set of negative polarity lines (polarity in the present context being only relative because RF current is passed through the coils 602). Each pair of positive and negative polarity windings may correspond to one period of alternating static magnetic field polarity (two opposed polarity magnets as in FIG. 5). It should be noted that the RF antenna is substantially longer in the longitudinal direction than the period (509 in FIG. 5) and that the position and number of wires in any of the coils 602 are selected to provide an approximate surface current density sinusoidally varying along the direction parallel to the surface of the magnets (500 in FIG. 5). Specific geometry will be shown later with reference to an orthogonal shimming design.

Figure 7:
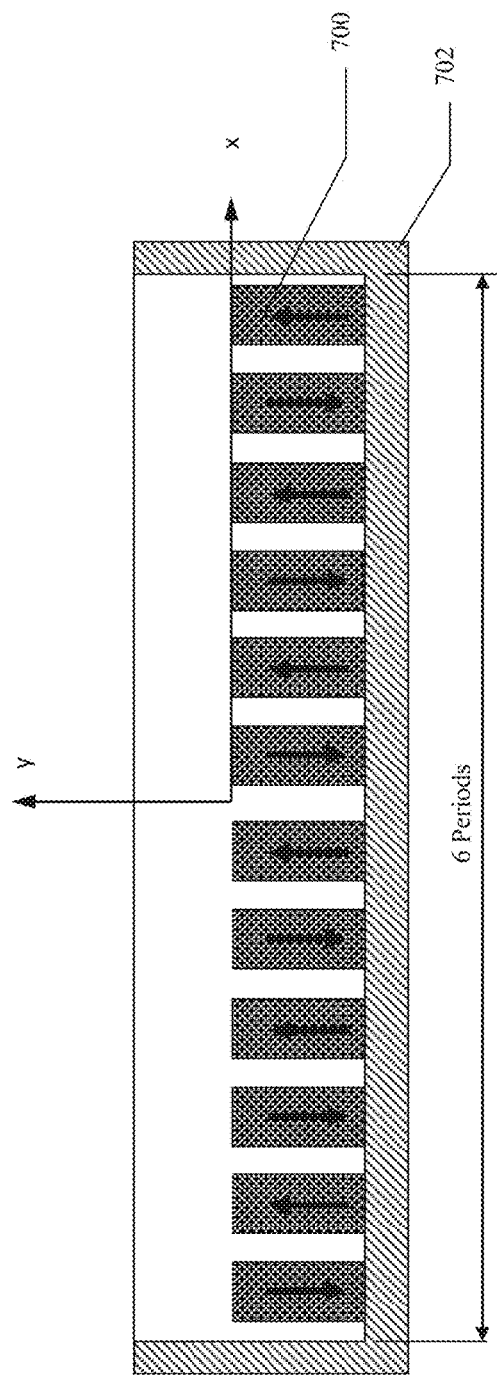
FIG. 7 shows an example periodic magnet arrangement.

FIG. 7 shows another possible arrangement of (permanent) magnets 700 having alternating polarity and disposed in a flux closure 702 such as may be made from steel or other magnetically permeable material. The magnet arrangement of FIG. 7 may be used with six multiples of the antenna arrangement of FIGS. 6A and 6B. It is contemplated that the length of the magnet arrangement consisting of six periods will be substantially longer than a region of interest in a sample disposed to the side of the magnets 700 so that the ROI (121 in FIG. 10) will be disposed in a static magnetic field having substantially equal amplitude along lines parallel to the surface of the magnets 700 for at least a known distance away from the surface of the magnets 700.

Figure 8:
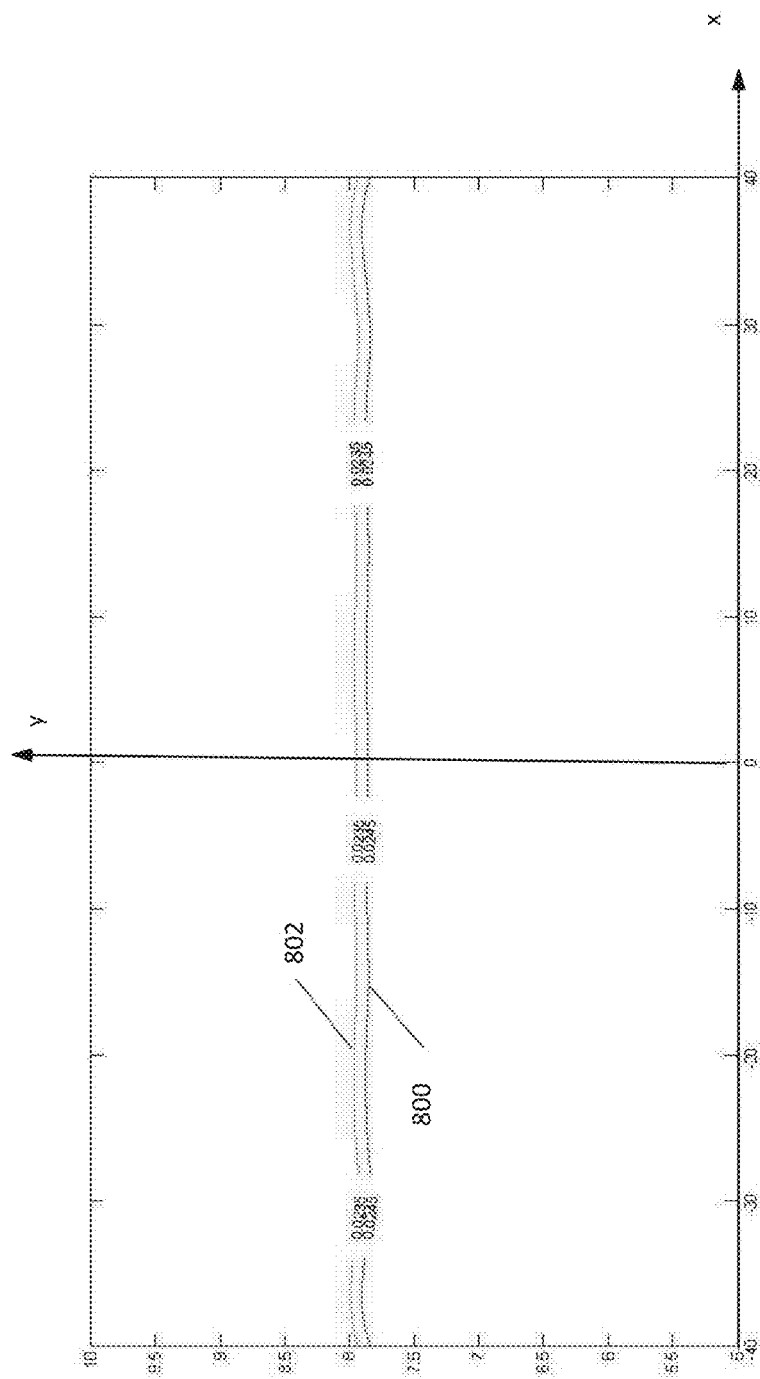
FIG. 8 shows static magnetic field amplitude of the example periodic magnet arrangement of FIG. 7 at two different distances from the magnets' surface.

FIG. 8 shows a graph of the static magnetic field amplitude along lines parallel to the surface of the magnets in FIG. 7 at two different distances, at 800 and 802, respectively. It may be observed in FIG. 8 that at any linear distance from the surface of the magnets (700 in FIG. 7) the static magnetic field amplitude is substantially constant, i.e., because the magnets in the example embodiment of FIG. 7 have flat surfaces, the static magnetic field is substantially flat along lines of equal amplitude at any selected distance from the surface of the magnets (700 in FIG. 7). Following is a list of materials and geometrical parameters that may be used in one example embodiment The permanent magnet material may be a rare-earth material such as neodymium iron boron NdFeB-35 having BHmax of 35 MGOe and residual induction Br=1.23 Tesla (12,300 Gauss). Embodiments of the flux closure (702 in FIG. 7) may be made from low carbon steel such as American National Standards Institute (ANSI) number 1008 Cold-Rolled Steel. The permanent magnets may be in the form of rectangular blocks about 10 mm high and 5 mm wide; the flux closure may be about 5 mm wide and 8 mm above the magnets' surface; the period is 15 mm wide. The same material properties will be used in all subsequently described examples.

A flat sample may be placed at about 8 mm distance from the surface of the magnets (700 in FIG. 7) between the line 802 and the line 800 corresponding to a static magnetic field amplitude of 0.0235 T and 0.0245 T, respectively. The RF resonant frequency at the foregoing static magnetic field amplitudes will be between 1 MHz and 1.04 MHz for hydrogen nuclei. By selecting a RF center resonance frequency of 1.02 MHz and a receiver bandwidth of 0.04 MHz, NMR signals will be excited substantially only between the line 802 and the line 800.

Figure 9:
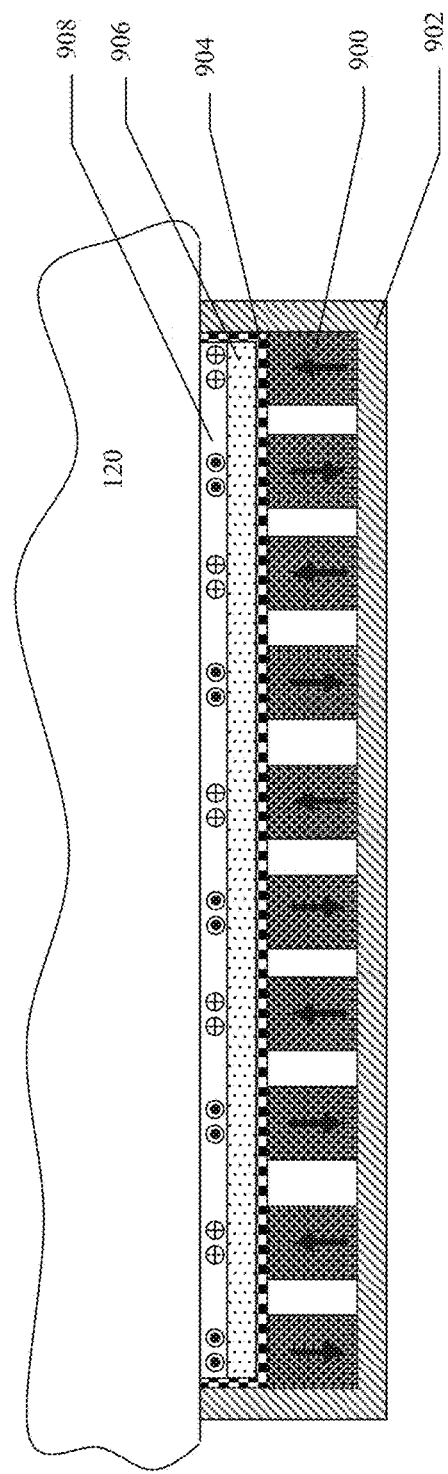
FIG. 9 shows a sample disposed to one side of a periodic magnet and antenna arrangement.

Another example embodiment of a NMR sensor using the principles explained with reference to FIGS. 5, 6A, 6B, 7 and 8 is shown in FIG. 9. The example embodiment in FIG. 9 may include a plurality of alternatingly, vertically polarized magnets 900 disposed in a flux closure 902 made from low carbon steel or other magnetically permeable material. The flux closure 902 may extend upwardly to cover the sides of the endmost magnets 900 as shown in FIG. 9. A radio frequency magnetic field shield 904 may be disposed above the magnets and be shaped to hold an antenna 908. The shield 904 may be made from electrically conductive, substantially non-magnetic material such as copper. The antenna 908 may be wound to provide 5 repetitions of the structure substantially as shown in FIG. 6B, and have 4 wires per period as will be further explained with reference to FIG. 13B, for example. The antenna 908 may be disposed above a layer of magnetically permeable material 906 such as ferrite or bounded metal powder, which will be further explained with reference to FIG. 20. A sample 120 of material to be analyzed is shown disposed on one side of the antenna 908. A region of investigation in which NMR phenomena are excited in the sample 120 and detected from the sample 120 will depend on the static magnetic field amplitude, the gradient of the static magnetic field, the frequency of the RF magnetic field, and the bandwidth of the RF magnetic field and the RF receiver (110 in FIG. 1). It is expected that the region of investigation (ROI—shown at 121 in FIG. 10) in the sample 120 may be approximately flat, rectangularly shaped and have a thickness that depends on the static magnetic field gradient and the RF bandwidths. The distance of the ROI from the edge of the sample 120 will depend on the RF frequency and the static magnetic field amplitude distribution for any assumed nucleus for which NMR phenomena are to be measured. It is contemplated that the nuclei for which NMR measurements are to be made will be hydrogen, however the scope of the present disclosure is not limited to experimentation using hydrogen nuclei.

Figure 10:
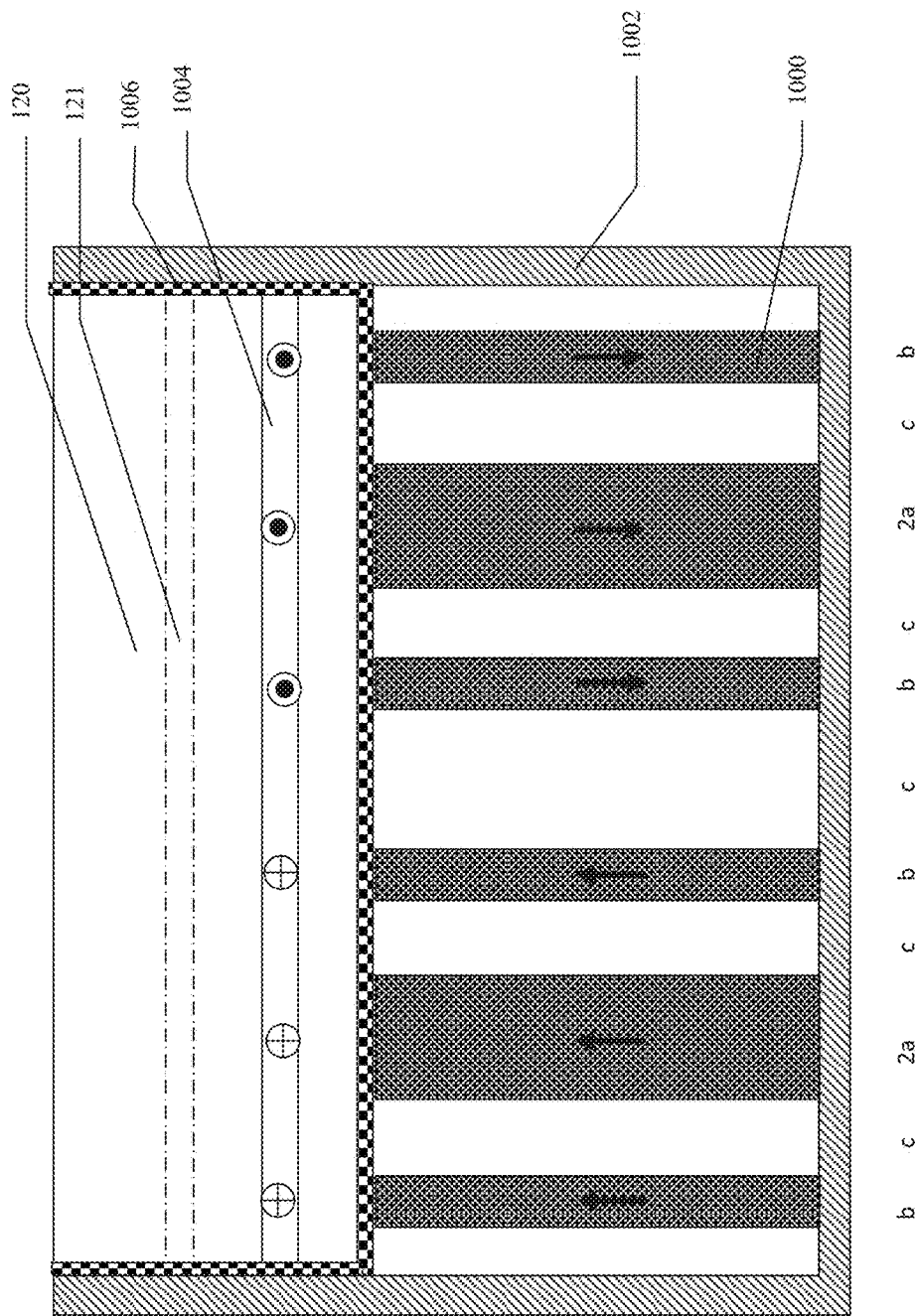
FIG. 10 shows another example periodic magnet and antenna arrangement, wherein a region of investigation is illustrated.

FIG. 10 shows another example embodiment of an NMR sensor having a plurality of magnets 1000 in sets of three, each having all its magnets being polarized in the same direction, with adjacent magnet sets being alternatingly polarized. An antenna 1004 may be wound, for example, as shown in FIG. 6B so that current flow through the antenna coils has polarity as shown in FIG. 10, wherein each polarity is associated with antenna coils above one of the magnet sets being polarized in one direction or the other. A radio frequency magnetic field shield 1006 may be disposed at the longitudinal ends of a sample chamber having a sample 120 of material to be analyzed therein. A region of investigation (ROI) 121 may be induced in the sample 120 based on criteria such as described with reference to FIG. 9. A flux closure 1002 may enclose the magnets 1000, the antenna 1004, the radio frequency magnetic field shield 1006, and the sample 120.

In the description of FIG. 5 it was explained that the static and RF magnetic fields can be presented in terms of harmonics. It is important that in selecting a structure for the permanent magnets and antennas that the first harmonic is not zero and the next few harmonics, preferably at least the second and third harmonics, are substantially zero. Higher order harmonics will decay in amplitude rapidly between the permanent magnet surface and the ROI 121 so as to have negligible amplitude in the ROI 121. FIG. 10 is an example of magnet blocks 1000 having uniform magnetization, but are composed from 3 individual blocks uniformly magnetized in one direction and the other 3 blocks being uniformly magnetized in the opposite direction. Positions of the magnet blocks and their dimensions are selected so that the first harmonic is not zero, the next five harmonics are zero, and all higher harmonics may be non-zero, but will decay in amplitude rapidly between the permanent magnet surface and the ROI 121 so as to be of negligible amplitude in the ROI 121. In FIG. 10, the width of the respectively alternatingly polarized magnets is shown as b and 2a. A distance between alternatingly polarized magnets is indicated by c. Using the foregoing notation and x=0 is selected at middle of magnet block being 2a wide, $$M_y = M_0 f(x) \quad (8)$$

$$f(x) = \begin{cases} 1 & 0 < x \le a \\ 0 & a < x \le a+c \\ 1 & a+c < x \le a+b+c \\ 0 & a+b+c < x \le a+b+2c \\ -1 & a+b+2c < x \le a+2b+2c \\ 0 & a+2b+2c < x \le a+2b+3c \\ -1 & a+2b+3c < x \le 3a+2b+3c \\ 0 & 3a+2b+3c < x \le 3a+2b+4c \\ -1 & 3a+2b+4c < x \le 3a+3b+4c \\ 0 & 3a+3b+4c < x \le 3a+3b+5c \\ 1 & 3a+3b+5c < x \le 3a+4b+5c \\ 0 & 3a+4b+5c < x \le 3a+4b+6c \\ 1 & 3a+4b+6c < x \le 4a+4b+6c \end{cases} \quad (9)$$

$$f(x+kT) = f(x)$$

As a result of the symmetric arrangement of the magnets 1000, there are only cosine terms and no sine terms in the expression f(x). The harmonics may be determined by the expressions below:

$$f_N(x) = \frac{c_0}{2} + \sum_{n=1}^{N} c_n \cos\left(\frac{2\pi n x}{T}\right) \quad (10)$$

$$c_n = \frac{2}{T} \int_0^T f(x) \cos\left(\frac{2\pi n x}{T}\right) dx$$

$$\begin{cases} c_{n=2k} = 0, k = 0, \pm 1, \pm 2, \dots \\ c_{n=2k+1} = \frac{4(-1)^{k+1}}{n\pi} \left[ \cos\left(\pi n \frac{2b/a + 3c/a}{4 + 4b/a + 6c/a}\right) + \cos\left(\pi n \frac{3c/a}{4 + 4b/a + 6c/a}\right) - \cos\left(\pi n \frac{2b/a + c/a}{4 + 4b/a + 6c/a}\right) \right] \end{cases}$$

wherein c3 and c5 can be made zero simultaneously when b/a=0.2362 and c/a=0.3451. Positions of antenna wires in the RF antenna shown in FIG. 10 may be selected so that the first harmonic is non-zero, the next five harmonics are zero, and all higher harmonics may be non-zero, but will decay in amplitude rapidly between the antenna surface and the ROI 121 so as to have negligible amplitude in the ROI 121.

Figure 11:
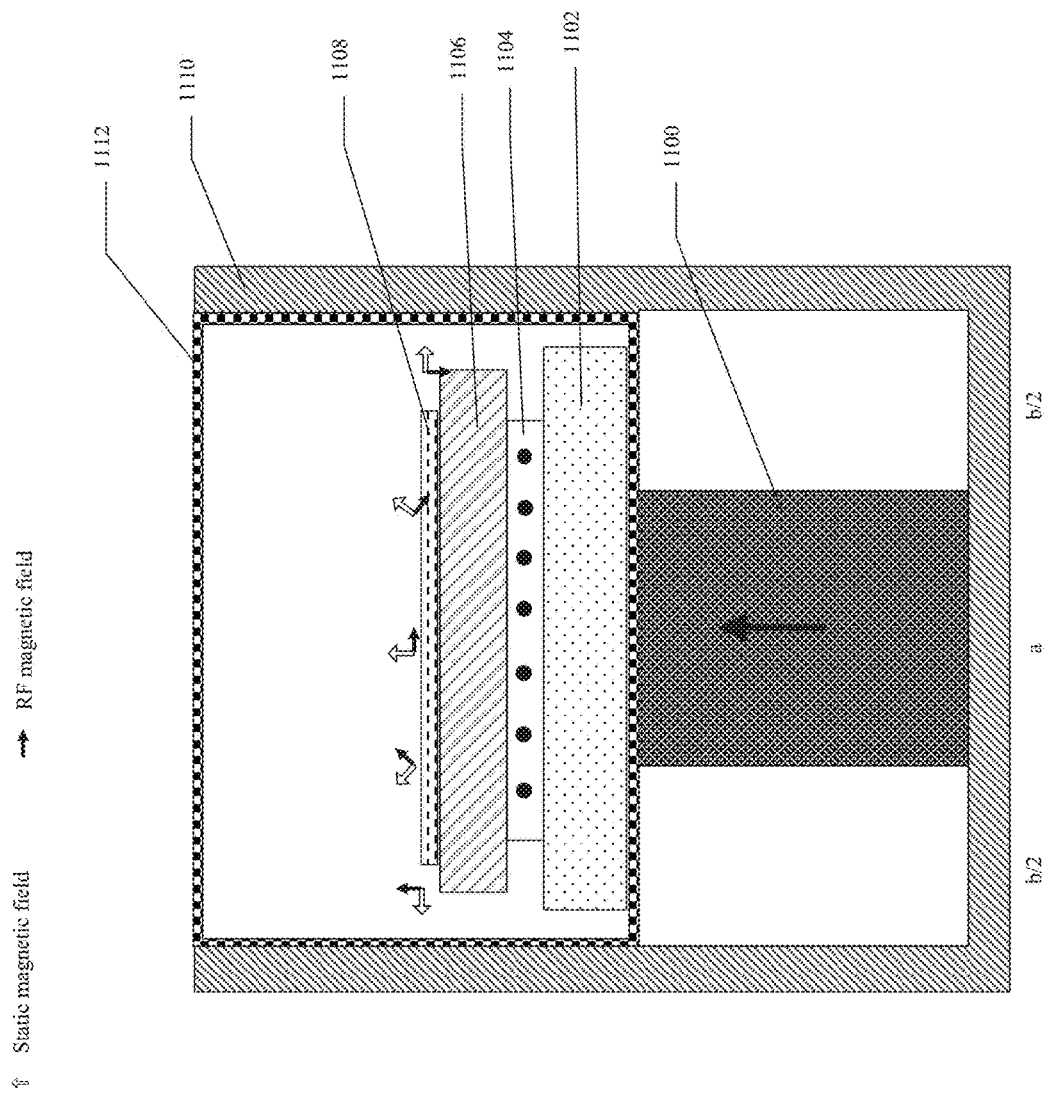
FIG. 11 shows another example embodiment of a magnet and antenna arrangement for imaging within a sample placed to one side of the magnet and antenna arrangement.

FIG. 11 shows another example embodiment of a sensor. A magnet 1100 may be disposed inside a flux closure 1110 made from low carbon steel or other highly magnetically permeable material. A radio frequency magnetic field shield may be defined by an enclosure 1112 in contact with one end of the magnet 1100, wherein the other end of the magnet 1100 is in contact with the flux closure 1110. The enclosure 1112 may be made from electrically conductive, non-magnetic material such as material such copper. The combination of the flux closure 1110 and the magnet 1100 polarized as shown may provide a static magnetic field having an amplitude which is substantially constant along lines of equal distance from the base of the base of the enclosure 1112 between the ends of the enclosure 1112 for at least a selected length. An antenna 1104 may be disposed between the base of the enclosure 1112 and a sample holder 1106. The antenna 1104 may be made using a plurality of electrical conductors extending transversely to the plane of the drawing and carrying RF current in the same polarity in each conductor. A magnetically permeable material plate 1102 such as made from ferrite or bonded metal powder may be disposed between the bottom of the shield 1112 and the antenna 1104. The static and RF magnetic field orientations are shown above a sample 1108 of material to be analyzed. The sample holder 1106 may be made from electrically non-conductive, non-magnetic material such as glass or plastic such as polystyrene. The magnet block 1100 width and position of wires in the RF antenna 1104 in the present example shown in FIG. 11 may be selected to have the first harmonic be non-zero, the next three harmonics being zero, and all higher harmonics may be non-zero, but will decay in amplitude rapidly between the magnet and antenna surfaces and the sample 1108 of material to be analyzed so as to have negligible amplitude in the sample 1108 of material to be analyzed. As will be explained with reference to FIG. 12 the width of the magnet shown may be equal to four times the distance between the edge of the magnet 1100 and the enclosure 1112 is indicated by b/2.

Figure 12:
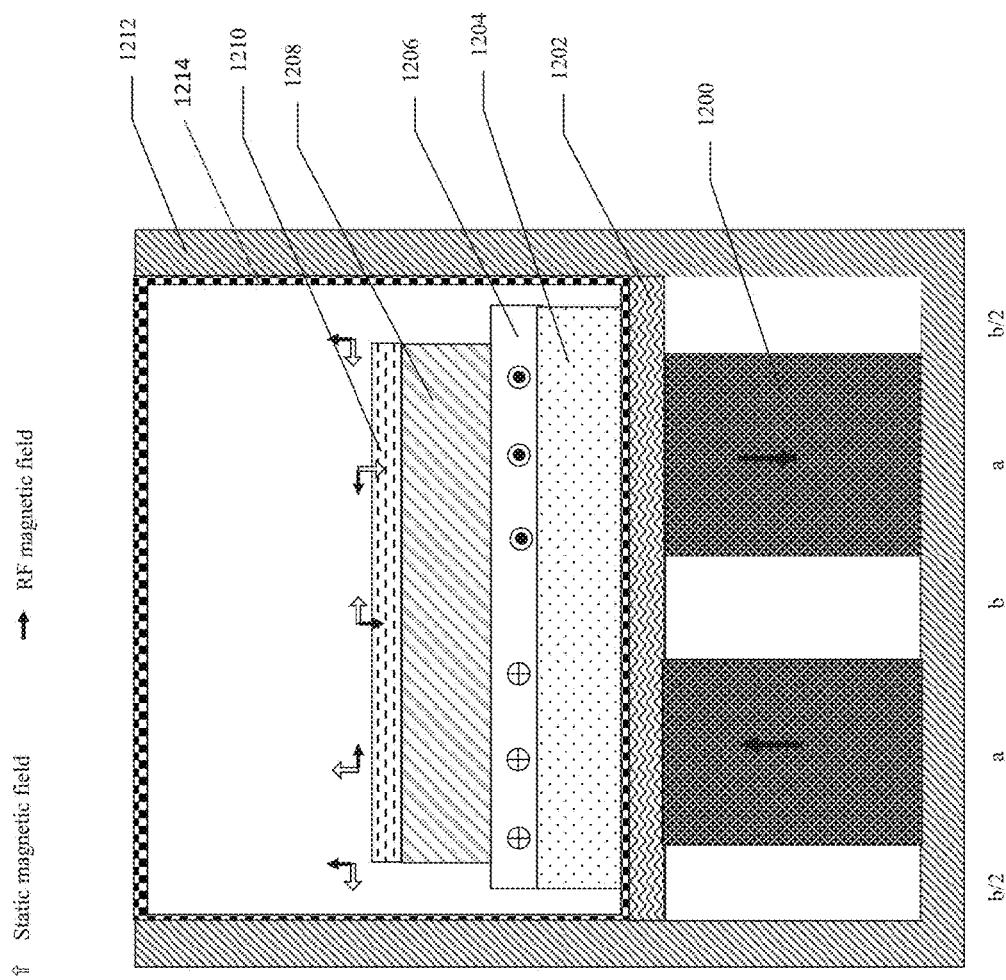
FIG. 12 shows another embodiment of a magnet and antenna arrangement for imaging a sample placed to one side thereof.
Figure 13A:
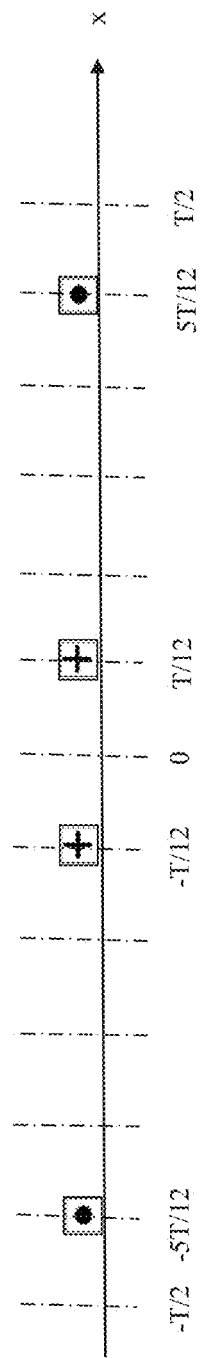

FIG. 12 shows another example embodiment having a pair of alternatingly polarized magnets 1200 disposed in a flux closure 1212 substantially as explained with reference to FIG. 11. An RF shield 1214, such as may be made from copper, may enclose an antenna 1206 having opposed polarity wires (e.g., a 3 full turn flat coil, see FIG. 6B) disposed above a ferrite plate 1204. Alternatively, the ferrite 1204 may be replaced by an electrically non-conductive and nonmagnetic antenna support such as may be made, for example, from glass or plastic. A sample holder 1208 and sample 1210 thereon are shown disposed above the antenna 1206. The polarization of the static and RF magnetic fields is shown by the solid and open arrows above the sample 1210. A region of investigation may be substantially flat, rectangularly shaped as explained above with reference to FIGS. 9 and 10. The example embodiment in FIG. 12 may include shimming electromagnets 1202 (operated, e.g., by the power supply shown at 105 in FIG. 1) to further refine the shape of the static magnetic field.

For the embodiments shown in FIGS. 11 and 12, a may represent the width of the magnet blocks and b may represent the spacing between the magnet blocks. Using the notation as in equation (9), $$f(x) = \begin{cases} 1 & 0 < x \le a/2 \\ 0 & a/2 < x \le a/2 + b \\ -1 & a/2 + b < x \le 3a/2 + b \\ 0 & 3a/2 + b < x \le 3a/2 + 2b \\ 1 & 3a/2 + 2b < x \le 2a + 2b \end{cases} \quad (11)$$

$$f(x + kT) = f(x)$$

Because of symmetry of the magnet arrangement and considering an origin of x in the center of the permanent magnet, there are no sine terms in the above expression, only cosine terms. The harmonics may be determined by the expression:

$$f_N(x) = \frac{c_0}{2} + \sum_{n=1}^{N} c_n \cos\left(\frac{2\pi n x}{T}\right) \quad (12)$$

$$c_n = \frac{2}{T}\int_0^T f(x)\cos\left(\frac{2\pi n x}{T}\right)dx$$

$$\begin{cases} c_{n=2k} = 0, k = 0, \pm 1, \pm 2, \dots \\ c_{n=2k-1} = \frac{4(-1)^{k+1}}{(2k-1)\pi}\cos\left[\frac{(2k-1)\pi}{2(a/b+1)}\right] \end{cases}$$

-continued $$f_N(x) = \frac{4}{\pi}\sum_{k=1}^{N}\frac{(-1)^{k+1}}{(2k-1)}\cos\left[\frac{(2k-1)\pi}{2(a/b+1)}\right]\cos\left[\frac{(2k-1)\pi}{a/b+1}\frac{x}{b}\right]$$

Using the above expression, c3=0 if a/b=2. Position of the wires in the RF antenna shown in FIG. 12 may be selected so that the first harmonic is non-zero, the next three harmonics are zero, and all higher harmonics may be non-zero, but will decay in amplitude rapidly between the antenna surface and the sample 1210 so as to be negligible amplitude in the sample 1210.

The above permanent magnet shimming was optimized for step-functions such as permanent magnet blocks or flat conductor antennas. In the case of wire-based electromagnet shims or RF antennas the step-function is replaced by the delta-function. FIGS. 13A, 13B, 13C and 13D provide details for examples of pure first and second order harmonics used for wire-based electromagnet orthogonal shimming.

Figure 14:
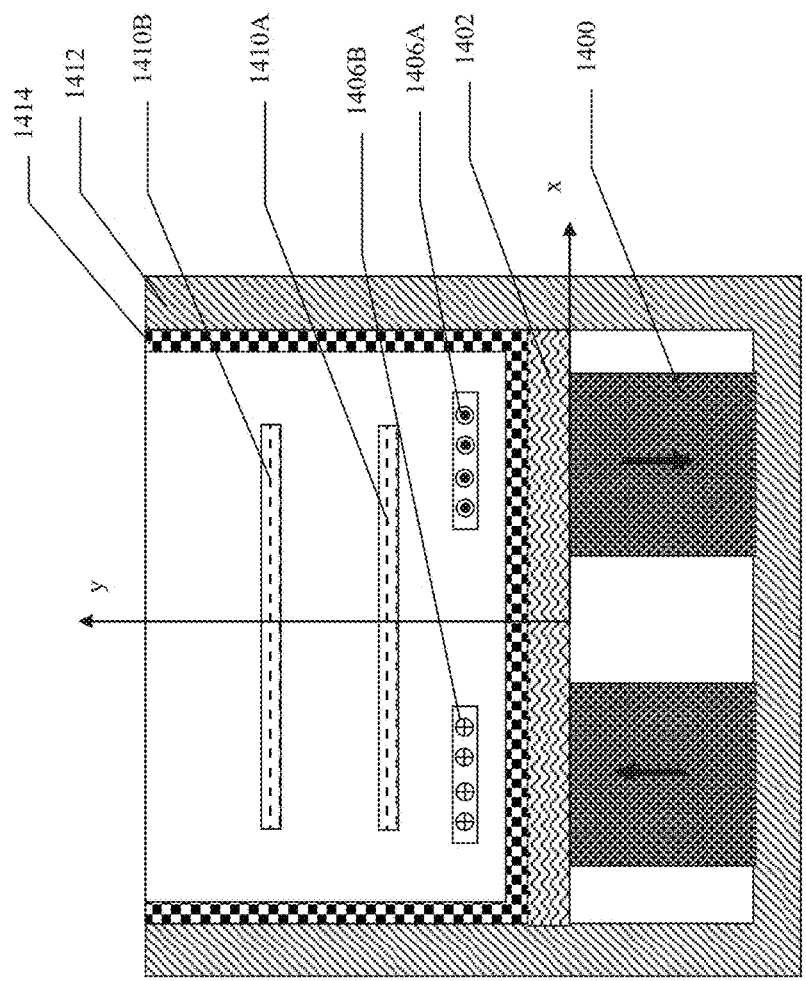
FIG. 14 shows an example sensor having shimmed permanent magnets.

FIGS. 14-18 present a specific example of one implementation as explained with reference to FIG. 12. Referring first to FIG. 14, another example embodiment of a sensor is shown which may have a pair of alternatingly polarized magnets 1400 disposed in a flux closure 1412 substantially as explained with reference to FIG. 12, but open at the top as shown in FIG. 14. An RF shield 1414, such as may be made from copper, may enclose an antenna having opposed polarity coils 1406A, 1406B (see FIG. 6B). A sample holder (not shown in FIG. 14, but it may be similar to the sample holder 1208 shown in FIG. 12) is disposed above the antenna. The polarization of the static and RF magnetic fields is substantially as shown in and as explained with reference to FIG. 12. A first region of investigation 1410A may be substantially flat and rectangularly shaped as explained above with reference to FIGS. 11 and 12. The example embodiment in FIG. 14 may include shimming electromagnets 1402 (operated, e.g., by the power supply shown at 105 in FIG. 1) to further refine the shape of the static magnetic field. A second region of investigation 1410B which may be obtained by appropriate selection of the RF magnetic field frequency and bandwidth and the RF receiver bandwidth is disposed at a different distance from the surface of the magnets 1400 than the first region of investigation (ROI) 1410A.

Referring to FIG. 3B, an example embodiment of a multilayer sample holder is shown at 300. The purpose of using such a sample holder 300 with magnets as shown in FIG. 2 is to increase the surface-to-volume ratio of a fluid sample. Making such a sample holder 300 may be performed as explained in the Martinez et al. publication cited above, by placing different capillary filters connecting a first layer 302 with other layers, shown at 304 to 310. Initially a multicomponent fluid is injected into the first layer 302, then using different capillary filters the fluid is divided into different layers 304 to 310 separated by stacking layers 312 of patterned paper each having distinct physical properties. Moreover, the surfaces of each layer 302 to 310 may be coated with a different coating material to interact differently with the same or different fluids. Being able to measure independently at each layer 302 to 310 may provide a so called "ELISA-array". The example sample holder shown in FIG. 3B may be used in connection with magnet and antenna arrangements as explained with reference to FIGS. 5 through 14 to be able to individually analyze each layer in a multiple layer sample.

Figure 15:
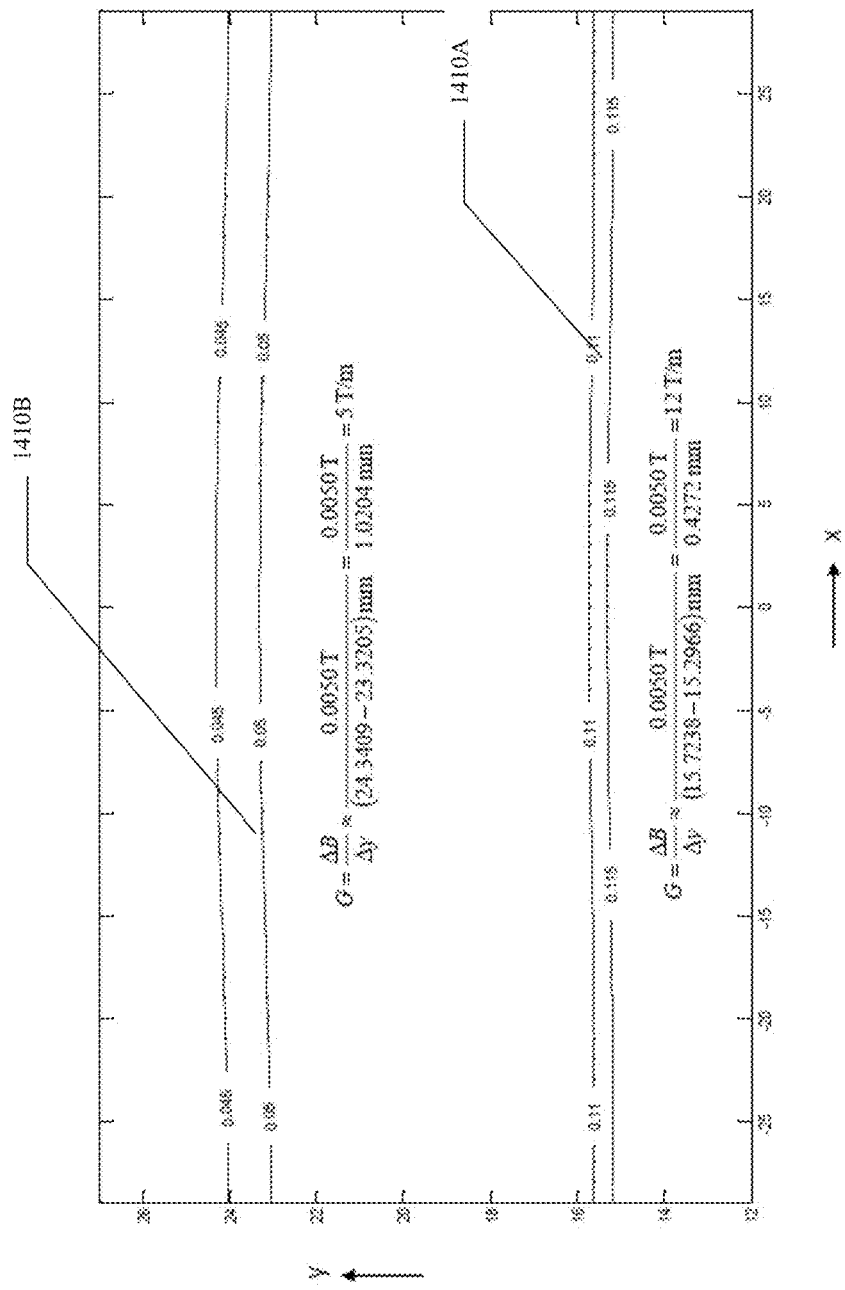
FIG. 15 shows an enlarged scale graph of the static magnetic field in two different regions of investigation generated using the embodiment of FIG. 14.
Figure 16:
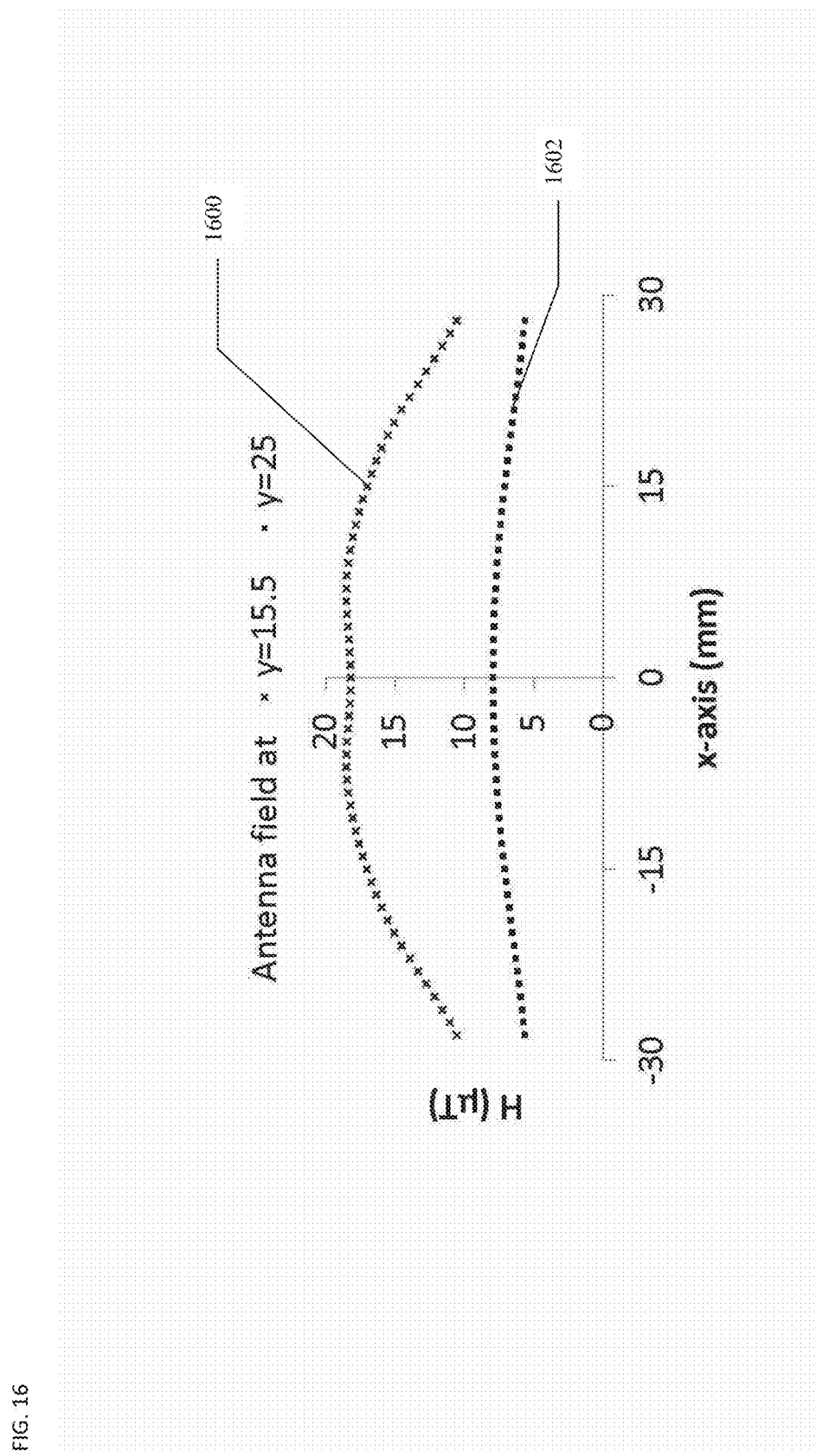
FIG. 16 shows an enlarged scale graph of the amplitude of the RF magnetic field in each respective ROI of FIG. 15.
Figure 17:
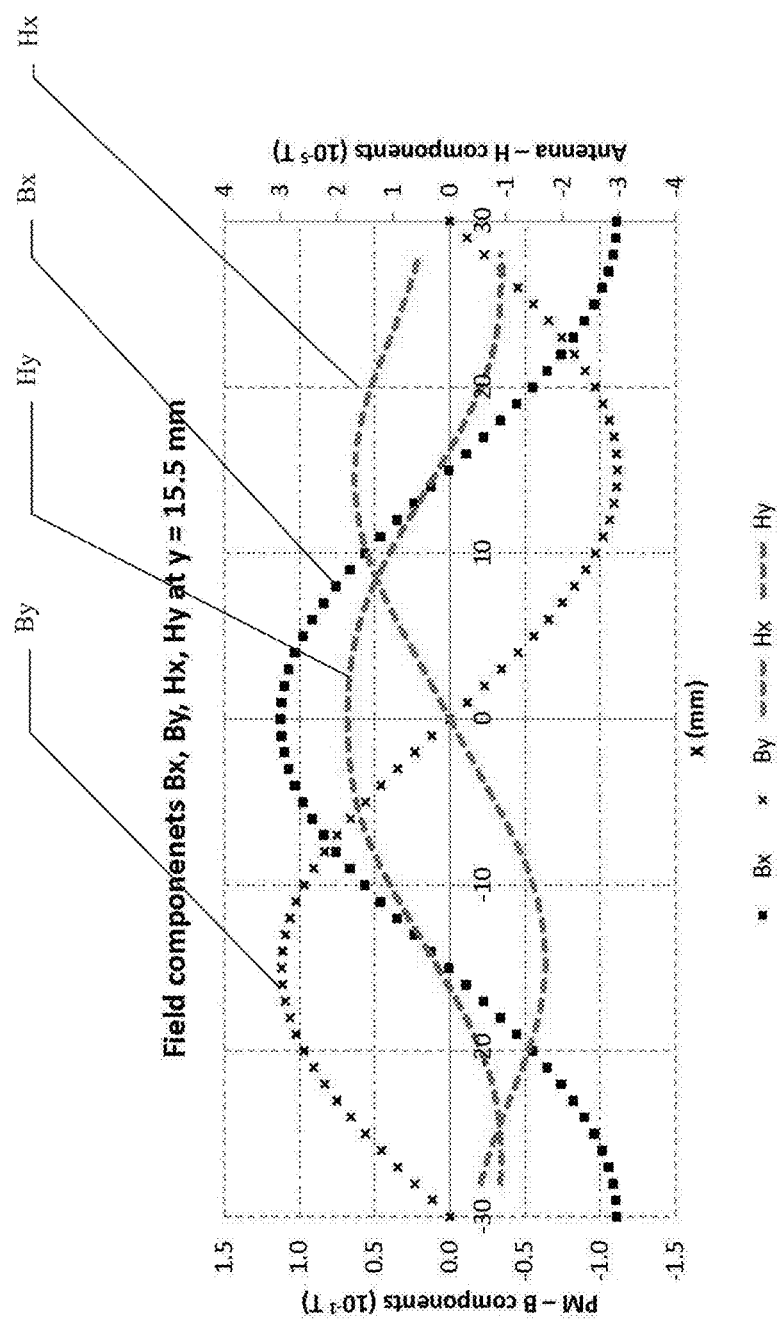
FIG. 17 shows a graph of the x and y components of the static (denoted by B) and RF (denoted by H) magnetic fields, respectively at Bx, By, and Hx, Hy for the magnet and RF antenna arrangement shown in FIG. 14.
Figure 18:
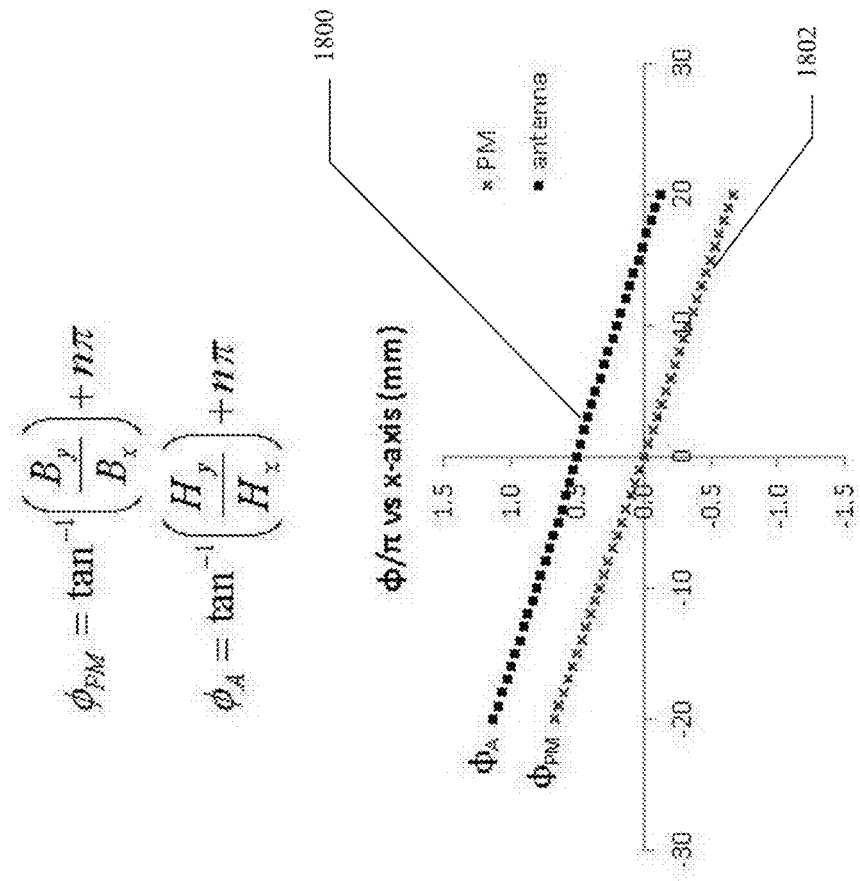
FIG. 18 shows a graph of the relative phase of each of the static and RF magnetic fields generated using the example embodiment of FIG. 14.

FIG. 15 shows an enlarged scale graph of the static magnetic field in the first ROI 1410A and second ROI 1410B, respectively. FIG. 16 shows an enlarged scale graph of the amplitude of the RF magnetic field per unit of current in each respective ROI at 1600 and 1602. FIG. 17 shows a graph of the x and y components of the static and RF magnetic fields, respectively at Bx, By, and Hx, Hy for the magnet and RF antenna arrangement shown in FIG. 14. FIG. 18 shows a graph of the relative phase of each of the static and RF magnetic fields generated using the example embodiment of FIG. 14 at 1800 and 1802, respectively.

Figure 19:
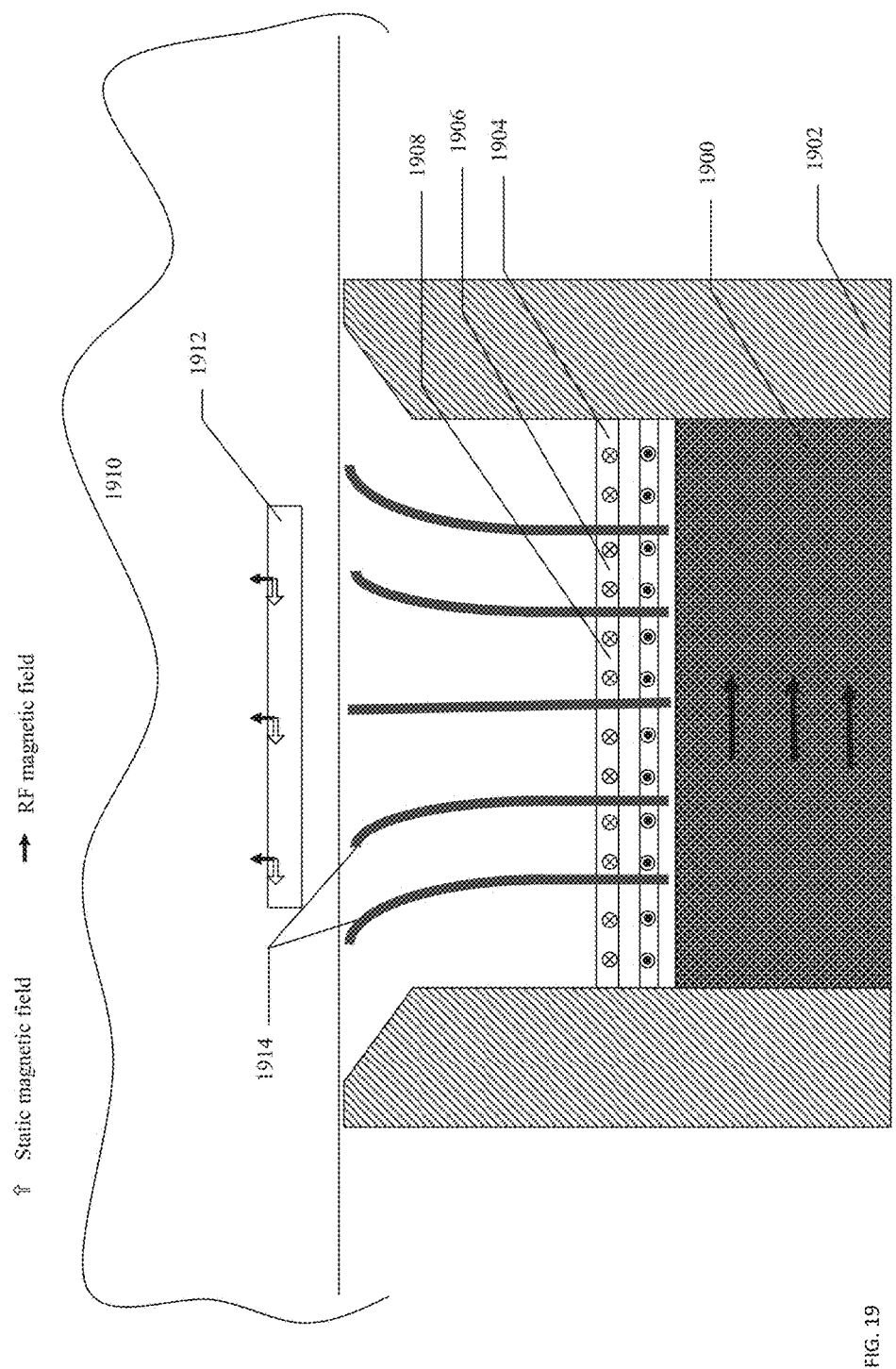
FIG. 19 shows another embodiment of a magnet and antenna arrangement for imaging a sample placed to one side thereof.

FIG. 19 shows another embodiment of a sensor. A magnet 1900 may be longitudinally polarized between flux path end plates 1902 made from low carbon steel or similar highly magnetically permeable material. A plurality of fins 1914 made from highly magnetically permeable material such as very low carbon steel (see the description above with reference to FIGS. 7 and 8 for example alloys) may be disposed along predetermined shapes corresponding to equal magnetic field scalar potential. Another definition may be that the fins represent a surface which is perpendicular to the static magnetic field direction at each point along the fin. A plurality of electromagnets, wound as solenoids 1904, 1906, 1908 having dipole moment substantially parallel to the polarization direction of the magnet 1900 may be disposed above the magnet 1900. All magnet assembly parameters are predetermined so that the desired static magnetic field will be generated in the ROI. However, manufacturing may not be perfect, the materials used may not be homogeneous thus having varying properties, and environmental interference with the magnetic field is possible. In the present embodiment the electromagnets 1904, 1906, 1908 are used to restore the predetermined magnetic field scalar potential at each fin. The RF antenna is omitted from FIG. 19 for clarity of the illustration, but it may be in the form of a solenoid wound so that its longitudinal axis is orthogonal to the polarization direction of the magnet 1900. The static magnetic field in a region of investigation ROI 1912 of a sample 1910 is homogeneous, uniform and in a direction parallel to the magnet 1900 polarization direction, and the RF magnetic field in the region of investigation ROI 1912 of a sample 1910 is homogeneous, uniform and in a direction perpendicular to the magnet 1900 polarization direction as shown by the open and solid arrows.

Figure 20:
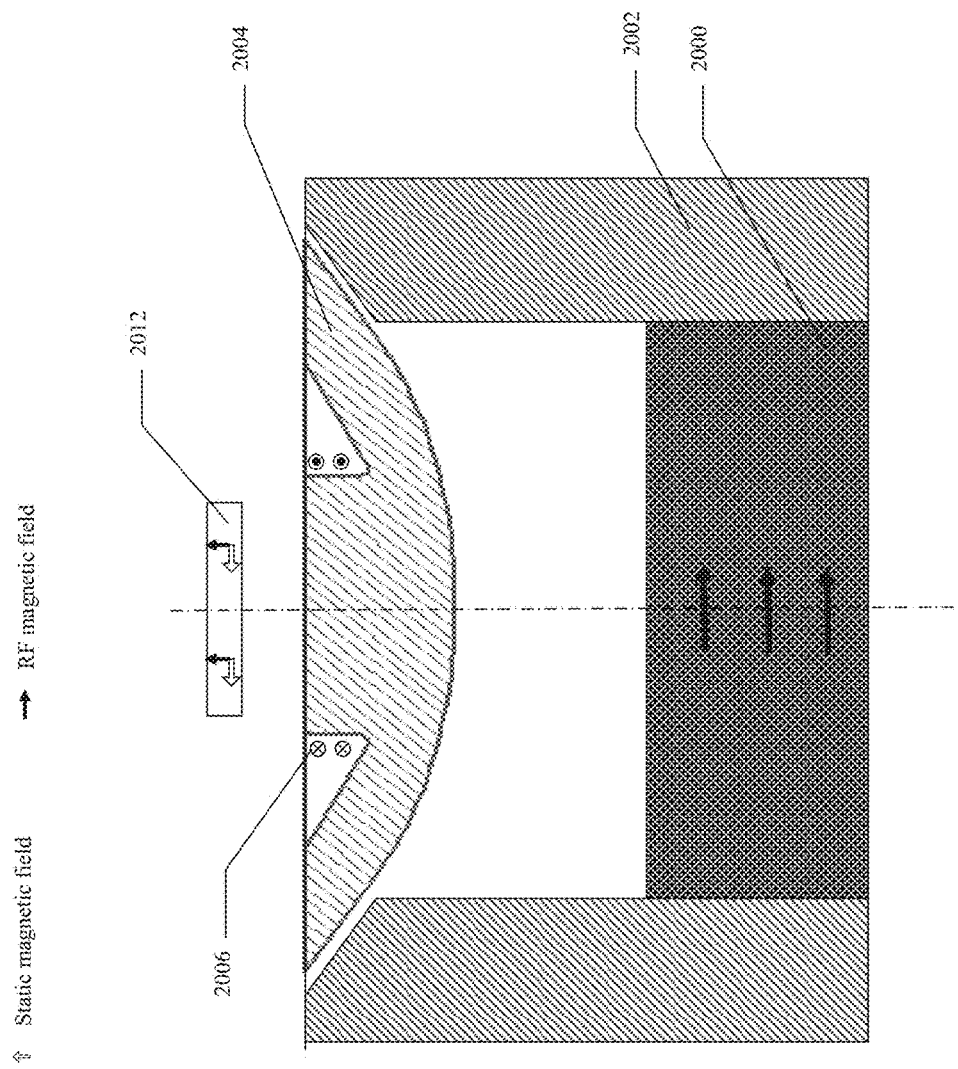
FIG. 20 shows another embodiment of a magnet and antenna arrangement for imaging a sample placed to one side thereof, including a structure for an antenna that may be used in the embodiment shown in FIG. 29.

A different aspect of the embodiment of FIG. 19 is shown in FIG. 20, wherein a magnet 2000 is disposed between flux path end plates 2002 substantially as in FIG. 19. A specially shaped ferrite or bonded metal powder pole piece 2004 shapes the RF magnetic fields to be oriented as shown by the open and solid arrows in a region of investigation (ROI) 2012 as shown. The antenna 2006 may be a solenoid coil as explained with reference to FIG. 19. The embodiment of FIG. 20 may omit the electromagnets shown in the embodiment of FIG. 19. The pole piece 2014 can be made from a soft ferrite material such as that sold under trade designation "F6" and manufactured by MMG-North America, 126 Pennsylvania Ave., Paterson, N.J., or another sold under trade designation "3C2" and manufactured by Philips, 230 Duffy Ave., Nicksville, N.Y. See, e.g., U.S. Pat. No. 5,698,979 issued to Taicher et al. Another example material for the pole piece 2014 may be a material as described in U.S. Pat. No. 6,452,388 issued to Reiderman et al. and entitled, "Ferromagnetic Metal Powder Combined with an Organic Nonconductive Binder."

Figure 3C:
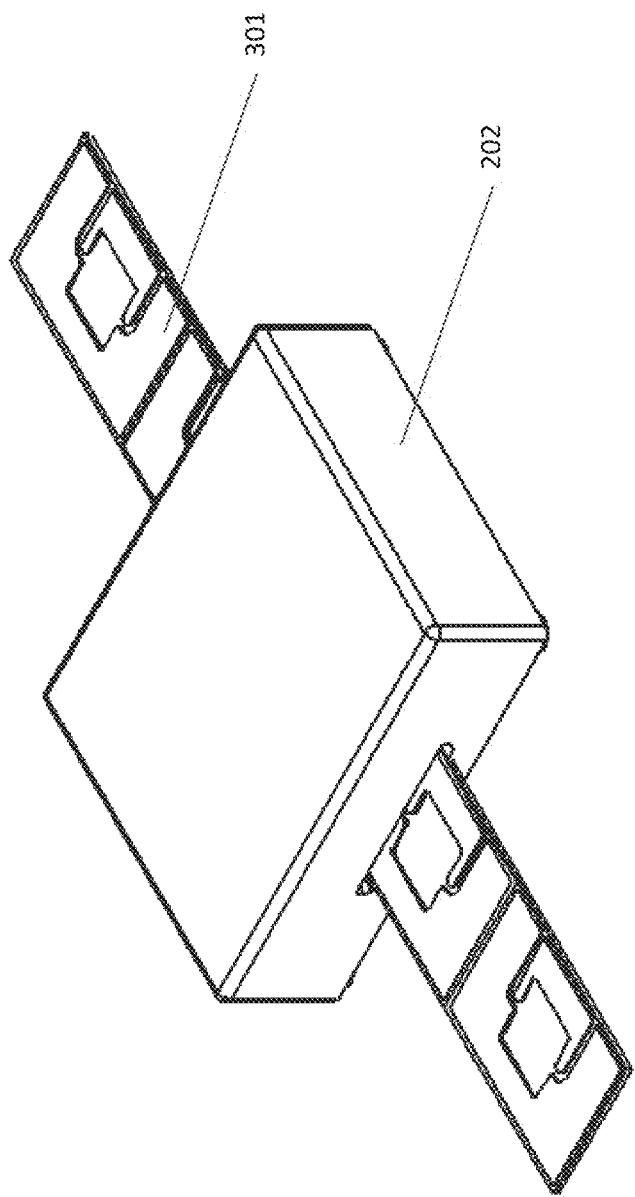
FIG. 3C shows an example embodiment of a multiple chamber microfluidic sample holder used in connection with an embodiment of a sensor according to the disclosure.

An example sample holder that may be used with sensor arrangements such as explained with reference to FIGS. 2, 4 19 and 20 may be better understood with reference to FIGS. 3C, 3D and 3E. A multiple sample holder 301 may be formed from a flat strip of plastic such as polystyrene. The multiple sample holder 301 may have a thickness and an internal sample chamber volume for each of a plurality of fluid samples (FIG. 3D) such that substantially all fluid in the respective sample chambers (FIGS. 3D and 3E) will be affected by surface contact phenomena. A sensor 202 may be configured substantially as explained with reference to FIG. 2 and connected to a measurement apparatus as explained with reference to FIG. 1. In FIG. 3C, the flat strip 320 may include a plurality of sample chambers 324 having dimensions as explained above. Each sample chamber 324 may be internally coated on its walls 322 during manufacture of the strip 320 with a selected analyte or reagent. A selected analyte or reagent, as the case may be, can be introduced, e.g., in the form of a fluid into each sample chamber through a respective fluid inlet 326. Displacement of air or gas in the sample chamber 324 prior to introduction of the selected analyte or reagent may take place through a corresponding fluid outlet 328. A top view of the example embodiment shown in FIG. 3D is shown in FIG. 3E. In the embodiment shown in FIGS. 3D and 3E, the sample chamber walls 322 may be substantially parallel and separated by a distance related to a size of the molecules in the reagent or analyte moved into the sample chamber 324 and a diffusion length of the molecules thereof.

Embodiments of a sample chamber, magnet and RF antenna coil(s) and/or RF shield according to the various aspects of the present disclosure may enable measurements of NMR signals from within a small number of molecular thicknesses from the surface defined by the boundaries of the sample chamber by suitable selection of static magnetic field gradient and associated RF magnetic field frequency, or, selecting an RF magnetic field bandwidth and receiver bandwidth so that the total NMR signal detected is from within a selected volume in the sample chamber, while surface and near surface NMR measurements may be made by selectively determining the signal content at RF frequencies within the received signal bandwidth that are associated with excitation of NMR phenomena at the static magnetic field amplitude and corresponding RF magnetic field frequency at positions proximate the surface(s) of the sample chamber. In some embodiments, by selecting a sample chamber to have a high surface to volume ratio, wherein surface affected NMR signals comprise a selected fraction of the total NMR signal, e.g., 25 to 50 percent, it may be possible to measure changes in surface relaxivity and diffusion constant substantially directly without the need to further analyze the NMR measurements with respect to position within the sample chamber.

Measurement of NMR signals from the entire sample chamber volume and from the near surface, irrespective of the sample chamber configuration and the measurement position within the sample volume may be made using well known RF pulsing sequences such as the CPMG (Carr-Purcell-Meiboom-Gill) sequence to determine relaxation times and diffusion coefficients of the materials being analyzed.

NMR methods for measuring presence of certain substances in a very small liquid sample may be based on simultaneously and optimally sensing T2 and T1 as described in U.S. Pat. Nos. 7,366,559, 7,355,360 and 7,355,402 issued to Taicher et al.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A nuclear magnetic resonance (NMR) apparatus, comprising:
   at least one magnet configured to induce a static magnetic field in a sample of material to be analyzed, wherein the sample is disposed on one side of the at least one magnet; and
   wherein the at least one magnet is configured such that the static magnetic field induced in the sample of material to be analyzed is substantially planar and has varying direction along surfaces of equal static magnetic field amplitude; and
   circuitry functionally connected to at least one radio frequency antenna, the circuitry having a selectable frequency and bandwidth such that NMR phenomena are excitable and detectable within regions of investigation having thickness and distance from a surface of the sample to be analyzed defined by the frequency and bandwidth for particular atomic nuclei within the sample to be analyzed.

2. The NMR apparatus of claim 1 wherein the magnet has a longitudinal axis; and wherein a direction of the static magnetic field within the sample in a plane perpendicular to the longitudinal axis varies periodically with respect to a position along a line at which the plane intersects the sample to be analyzed.

3. The NMR apparatus of claim 2 wherein a gradient of the amplitude of the static magnetic field within the sample is perpendicular to the longitudinal axis.

4. The NMR apparatus of claim 2 wherein the at least one magnet comprises a plurality of alternatingly polarized magnets bounded by a flux closure on a side opposite to the side wherein the sample to be analyzed is disposed, the alternatingly polarized magnets polarized in directions perpendicular to the longitudinal axis and toward and away from the sample of material to be analyzed.

5. The NMR apparatus of claim 4 further comprising at least one radio frequency antenna configured to induce a radio frequency magnetic field in the sample of material to be analyzed and wherein the at least one radio frequency antenna is disposed between the at least one magnet and the sample of material to be analyzed.

6. The NMR apparatus of claim 5 wherein the at least one radio frequency antenna comprises a plurality of alternating polarized wires extending in a direction parallel to the longitudinal axis.

7. The NMR apparatus of claim 5 further comprising a radio frequency magnetic field shield disposed between the at least one magnet and the least one radio frequency antenna.

8. The NMR apparatus of claim 5 further comprising a magnetically permeable material disposed to a first side of the at least one radio frequency antenna opposite to a second side wherein the sample to be analyzed is disposed.

9. The NMR apparatus of claim 4 wherein a width of each of the plurality of magnets and a spacing between adjacent ones of the plurality of magnets is such that a first harmonic of the polarization direction of the static magnetic field with respect to position along the plurality of magnets is non zero and at least a second and third harmonic of the polarization direction of the static magnetic field are substantially zero.

10. The NMR apparatus of claim 4 further comprising a plurality of shimming electromagnets disposed between the at least one magnet and the sample.

11. The NMR apparatus of claim 10 wherein the plurality of shimming electromagnets comprises a plurality of alternating polarized wires extending in a direction parallel to the longitudinal axis.

12. The NMR apparatus of claim 11 wherein a position of each of the plurality of wires and a direct current in each of the plurality of wires is such that a first harmonic of the polarization direction of the static magnetic field with respect to position along the plurality of magnets is non zero and at least a second and third harmonic of the polarization direction of the static magnetic field are substantially zero.

13. The NMR apparatus of claim 10 wherein the plurality of shimming electromagnets are arranged to orthogonally shim the at least one magnet.

14. The NMR apparatus of claim 1 wherein a gradient of an amplitude of the static magnetic field within the sample of material to be analyzed is homogeneous.

15. The NMR apparatus of claim 1 wherein a gradient of an amplitude of the static magnetic field within the sample is uniform.

16. The NMR apparatus of claim 1 further comprising a sample chamber comprising a plurality of substantially planar layers each disposed in a part of the static magnetic field having substantially equal amplitude and wherein each layer has a different value of static magnetic field amplitude.

17. The NMR apparatus of claim 1 further comprising at least one radio frequency antenna configured to induce a radio frequency magnetic field in the sample of material to be analyzed and wherein the sample of material to be analyzed is disposed on one side of the at least one radio frequency antenna.

18. The NMR apparatus of claim 17 wherein the radio frequency magnetic field is substantially orthogonal to the static magnetic field within the sample of material to be analyzed.

19. The NMR apparatus of claim 17 further comprising a radio frequency magnetic field shield disposed between the at least one magnet and the least one radio frequency antenna.

20. The NMR apparatus of claim 19 wherein the radio frequency magnetic field shield encloses the least one radio frequency antenna.

21. The NMR apparatus of claim 17 further comprising a magnetically permeable material disposed to a first side of the at least one radio frequency antenna opposite to a second side wherein the sample of material to be analyzed is disposed.

22. The NMR apparatus of claim 21 wherein the magnetically permeable material comprises at least one of ferrite and a ferromagnetic metal powder combined with an organic, electrically non-conductive binder.

23. The NMR apparatus of claim 1 further comprising at least one radio frequency antenna enclosing the sample of material to be analyzed.

24. The NMR apparatus of claim 1 further comprising at least one shimming magnet disposed between the at least one magnet and the sample to be analyzed.

25. The NMR apparatus of claim 1 wherein the particular atomic nuclei comprise hydrogen nuclei.

26. The NMR apparatus of claim 1 wherein the circuitry is configured to perform Carr Purcell Meiboom Gill spin echo NMR excitation and detection sequences in the sample to be analyzed.

27. A nuclear magnetic resonance (NMR) apparatus, comprising:
   at least one magnet configured to induce a static magnetic field in a sample of material to be analyzed;

at least one radio frequency antenna configured to induce a radio frequency magnetic field in the sample of material to be analyzed, wherein the least one magnet and the at least one radio frequency antenna are disposed on one side of the sample; and wherein the at least one magnet is polarized in a direction transverse to a direction toward the sample to be analyzed, and a flux closure bounds both longitudinal ends of the at least one magnet.

28. The NMR apparatus of claim 27 further comprising a plurality of fins disposed between the at least one magnet and the sample to be analyzed, each of the plurality of fins made from a magnetically permeable material and having a shape corresponding to a surface of equal static magnetic field scalar potential.

29. The NMR apparatus of claim 28 further comprising a plurality of shimming electromagnets disposed between the fins and between the flux closure and the fins on both ends of the at least one magnet.

30. The NMR apparatus of claim 27 further comprising circuitry functionally connected to the at least one radio frequency antenna, the circuitry having a selectable frequency and bandwidth such that NMR phenomena are excitable and detectable within regions of investigation having thickness and distance from a surface of the sample to be analyzed defined by the frequency and bandwidth for particular atomic nuclei within the sample to be analyzed.

31. The NMR apparatus of claim 30 wherein the particular atomic nuclei comprise hydrogen nuclei.

32. The NMR apparatus of claim 30 wherein the circuitry is configured to perform Carr Purcell Meiboom Gill spin echo NMR excitation and detection sequences in the sample to be analyzed.

33. A method for nuclear magnetic resonance (NMR) measurement, comprising:
inducing a static magnetic field in a sample of material to be analyzed, the static magnetic field being substantially planar and having varying direction along lines of equal amplitude of the static magnetic field, the inducing the static magnetic field originating on one side of the sample of material to be analyzed;

inducing a radio frequency magnetic field in the sample of material to be analyzed, the radio frequency magnetic field being substantially orthogonal to the static magnetic field; and detecting NMR phenomena excited in the sample of material to be analyzed, wherein the inducing the radio frequency magnetic field is performed at a selectable frequency and bandwidth such that NMR phenomena are excitable and detectable within regions of investigation having thickness and distance from a surface of the sample to be analyzed defined by the frequency and bandwidth for particular atomic nuclei within the sample to be analyzed.

34. The method of claim 33 further comprising shimming the static magnetic field.

35. The method of claim 33 further comprising shielding the radio frequency magnetic field from a means for inducing the static magnetic field.

36. The method of claim 33 wherein the static magnetic field has a direction corresponding to a periodic function with respect to a position about a means for inducing the static magnetic field.

37. The method of claim 36 wherein a first harmonic of the periodic function in a sample of material to be analyzed is non-zero, and at least a second and a third harmonic thereof are substantially zero.

38. The method of claim 37 wherein the second and third harmonics of the periodic function are further reduced by orthogonal shimming of the static magnetic field.

39. The method of claim 33 wherein the sample of material to be analyzed is separated into a plurality of substantially flat layers each disposed in a part of the static magnetic field having a different amplitude, and detecting NMR phenomena separately from each of the plurality of layers by selecting a frequency of the radio frequency magnetic field corresponding to the static magnetic field amplitude in each of the plurality of layers.

* * * * *